United States Patent
Alvez-Manoli

(10) Patent No.: US 11,850,576 B2
(45) Date of Patent: *Dec. 26, 2023

(54) ACIDIC AROMATIZATION CATALYSTS WITH IMPROVED ACTIVITY AND SELECTIVITY

(71) Applicant: Chevron Phillips Chemical Company LP, The Woodlands, TX (US)

(72) Inventor: Gabriela D. Alvez-Manoli, Kingwood, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/676,290

(22) Filed: Feb. 21, 2022

(65) Prior Publication Data

US 2022/0176356 A1 Jun. 9, 2022

Related U.S. Application Data

(60) Continuation of application No. 16/720,097, filed on Dec. 19, 2019, now Pat. No. 11,291,978, which is a division of application No. 15/697,735, filed on Sep. 7, 2017, now Pat. No. 10,556,228.

(60) Provisional application No. 62/384,746, filed on Sep. 8, 2016.

(51) Int. Cl.
| | |
|---|---|
| *B01J 29/62* | (2006.01) |
| *B01J 29/068* | (2006.01) |
| *B01J 37/02* | (2006.01) |
| *C07C 5/41* | (2006.01) |
| *B01J 27/10* | (2006.01) |
| *B01J 27/12* | (2006.01) |
| *B01J 37/26* | (2006.01) |
| *B01J 37/24* | (2006.01) |
| *B01J 37/00* | (2006.01) |
| *B01J 27/13* | (2006.01) |

(52) U.S. Cl.
CPC ............ *B01J 29/068* (2013.01); *B01J 27/10* (2013.01); *B01J 27/12* (2013.01); *B01J 29/62* (2013.01); *B01J 37/0009* (2013.01); *B01J 37/0201* (2013.01); *B01J 37/0246* (2013.01); *B01J 37/24* (2013.01); *B01J 37/26* (2013.01); *C07C 5/41* (2013.01); *B01J 27/13* (2013.01); *B01J 2229/20* (2013.01); *B01J 2229/42* (2013.01); *C07C 2529/068* (2013.01); *C07C 2529/62* (2013.01); *C10G 2300/70* (2013.01)

(58) Field of Classification Search
CPC ...... B01J 29/068; B01J 29/62; B01J 2229/20; B01J 2229/42; B01J 27/10; B01J 27/12; B01J 27/13; B01J 37/0009; B01J 37/24; B01J 37/04; B01J 37/02; B01J 37/0246; B01J 37/08; C07C 5/41; C07C 5/417; C07C 2529/068; C07C 2529/62; C10G 2300/70
USPC ............... 502/60, 63, 64, 66, 69, 74, 85
See application file for complete search history.

(56) References Cited

U.S. PATENT DOCUMENTS

| | | | |
|---|---|---|---|
| 3,849,290 A | 11/1974 | Wise | |
| 4,104,320 A | 8/1978 | Bernard | |
| 4,456,527 A | 6/1984 | Buss et al. | |
| 4,808,295 A | 2/1989 | Nemet-Mavrodin | |
| 4,861,932 A | 8/1989 | Chen | |
| 4,954,245 A | 9/1990 | Miller | |
| 5,196,631 A | 3/1993 | Murakawa | |
| 5,207,042 A * | 5/1993 | Molinar | E04B 1/10 52/92.1 |
| 5,247,178 A | 9/1993 | Ury | |
| 5,314,854 A | 5/1994 | Galperin | |
| 5,389,235 A | 2/1995 | Russ | |
| 5,401,365 A | 3/1995 | Chen | |
| 5,401,386 A | 3/1995 | Morrison | |
| 5,507,939 A | 4/1996 | Russ | |
| 5,520,798 A | 5/1996 | Innes | |
| 5,879,538 A | 3/1999 | Haritatos | |
| 5,914,028 A | 6/1999 | Wilson | |
| 5,980,731 A | 11/1999 | Kao | |
| 6,143,166 A | 11/2000 | Nacamuli | |
| 6,190,539 B1 | 2/2001 | Holtermann | |
| 6,207,042 B1 | 3/2001 | Holtermann | |
| 6,406,614 B1 | 6/2002 | Tiedtke | |
| 6,458,736 B2 | 10/2002 | Mohr | |
| 6,518,470 B1 | 2/2003 | Fukunaga | |
| 6,812,180 B2 | 11/2004 | Fukunaga | |
| 7,153,801 B2 | 12/2006 | Wu | |
| 7,932,425 B2 | 4/2011 | Blessing | |

(Continued)

FOREIGN PATENT DOCUMENTS

| | | |
|---|---|---|
| EP | 191212 A | 8/1986 |
| EP | 0201856 B1 | 1/1991 |
| EP | 1038579 A1 | 9/2000 |

OTHER PUBLICATIONS

Fukunaga et al., "Halogen-promoted Pt/KL Zeolite Catalyst for the Production of Aromatic Hydrocarbons from Light Naphtha," Catal. Surv. Asia (2010) 14:96-102.

Jentoft et al., "Platinum Clusters Supported in Zeolite LTL: Influence of Catalyst Morphology on Performance in n-Hexane Reforming," Journal of Catalysis, 179 (1998) pp. 565-580.

(Continued)

*Primary Examiner* — Elizabeth D Wood
(74) *Attorney, Agent, or Firm* — Merchant & Gould P.C.

(57) ABSTRACT

Methods for producing supported catalysts containing a transition metal and a bound zeolite base are disclosed. These methods employ a step of impregnating the bound zeolite base with the transition metal, fluorine, and high loadings of chlorine. The resultant high chlorine content supported catalysts have improved catalyst activity in aromatization reactions.

20 Claims, 10 Drawing Sheets

(56) References Cited

U.S. PATENT DOCUMENTS

| | | |
|---|---|---|
| 8,664,145 B2 | 3/2014 | Wu |
| 8,716,161 B2 | 5/2014 | Wu |
| 8,835,341 B2 | 9/2014 | Khare |
| 8,912,108 B2 | 12/2014 | Wu |
| 10,556,228 B2 * | 2/2020 | Alvez-Manoli ...... B01J 37/0201 |
| 2004/0259719 A1 | 12/2004 | Wu |
| 2010/0160150 A1 | 6/2010 | Wu |
| 2013/0231511 A1 * | 9/2013 | Wu .................. B01J 37/24 |
| | | 585/407 |
| 2013/0231512 A1 | 9/2013 | Wu |
| 2014/0088333 A1 | 3/2014 | Khare |
| 2014/0213839 A1 | 7/2014 | Wu |

OTHER PUBLICATIONS

Sugimoto et al. "Electronic state of platinum supported on the monochlorotrifluoromethane-treated alkaline L zeolite," Applied Catalysis A: General, 102 (1993) pp. 167-180.

* cited by examiner

ACIDIC AROMATIZATION CATALYSTS WITH IMPROVED ACTIVITY AND SELECTIVITY

REFERENCE TO RELATED APPLICATION

This application is a continuation application of U.S. patent application Ser. No. 16/720,097, filed on Dec. 19, 2019, now U.S. Pat. No. 11,291,978, which is a divisional application of U.S. patent application Ser. No. 15/697,735, filed on Sep. 7, 2017, now U.S. Pat. No. 10,556,228, which claims the benefit of U.S. Provisional Patent Application No. 62/384,746, filed on Sep. 8, 2016, the disclosures of which is are incorporated herein by reference in their entirety.

FIELD OF THE INVENTION

The present disclosure concerns methods for producing supported catalysts, and more particularly relates to the production of supported aromatization catalysts containing a transition metal and a bound zeolite base using a catalyst impregnation step in which high loadings of chlorine are present.

BACKGROUND OF THE INVENTION

The catalytic conversion of non-aromatic hydrocarbons into aromatic compounds, often referred to as aromatization or reforming, is an important industrial process that may be used to produce benzene, toluene, xylenes, and the like. The aromatization or reforming process often is conducted in a reactor system that may contain one or more reactors containing transition metal based catalysts. These catalysts may increase the selectivity to and/or the yield of the desired aromatic compounds. These catalysts also slowly lose their activity over time, often indicated by a loss of the selectivity to desired aromatic compounds and/or a reduction in conversion rates.

It would be beneficial to have an improved aromatization catalyst that offers high catalyst activity and selectivity, low fouling rates, and stability over long production runs. Accordingly, it is to these ends that the present disclosure is principally directed.

SUMMARY OF THE INVENTION

Supported catalysts that may be used in aromatization processes are disclosed and described herein. In one aspect, such catalysts may comprise a bound zeolite base and, based on the total weight of the supported catalyst, from about 0.3 wt. % to about 3 wt. % of a transition metal, from about 1.8 wt. % to about 4 wt. % of chlorine, and from about 0.4 wt. % to about 1.5 wt. % of fluorine. Often, these supported catalysts may be characterized by a peak reduction temperature on a Temperature Programmed Reduction curve in a range from about 580° F. to about 800° F.

Methods for producing supported catalysts also are disclosed and described herein. One such method for producing a supported catalyst may comprise (a) impregnating a bound zeolite base with a transition metal precursor, a chlorine precursor, and a fluorine precursor to form an impregnated zeolite base; and (b) drying and then calcining the impregnated zeolite base to produce the supported catalyst. The supported catalyst generally comprises from about 0.3 wt. % to about 3 wt. % of a transition metal, from about 1.8 wt. % to about 4 wt. % of chlorine, and from about 0.4 wt. % to about 1.5 wt. % of fluorine, based on the total weight of the supported catalyst. The supported catalyst may be characterized by a peak reduction temperature on a Temperature Programmed Reduction curve in a range from about 580° F. to about 800° F.

Supported catalysts produced by the methods provided herein may be used in aromatization processes to produce aromatic compounds from non-aromatic hydrocarbons. Such catalysts may have the unexpected combination of increased catalyst activity and reduced fouling rates, while maintaining excellent selectivity (e.g., to benzene and toluene).

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

Figure 1:
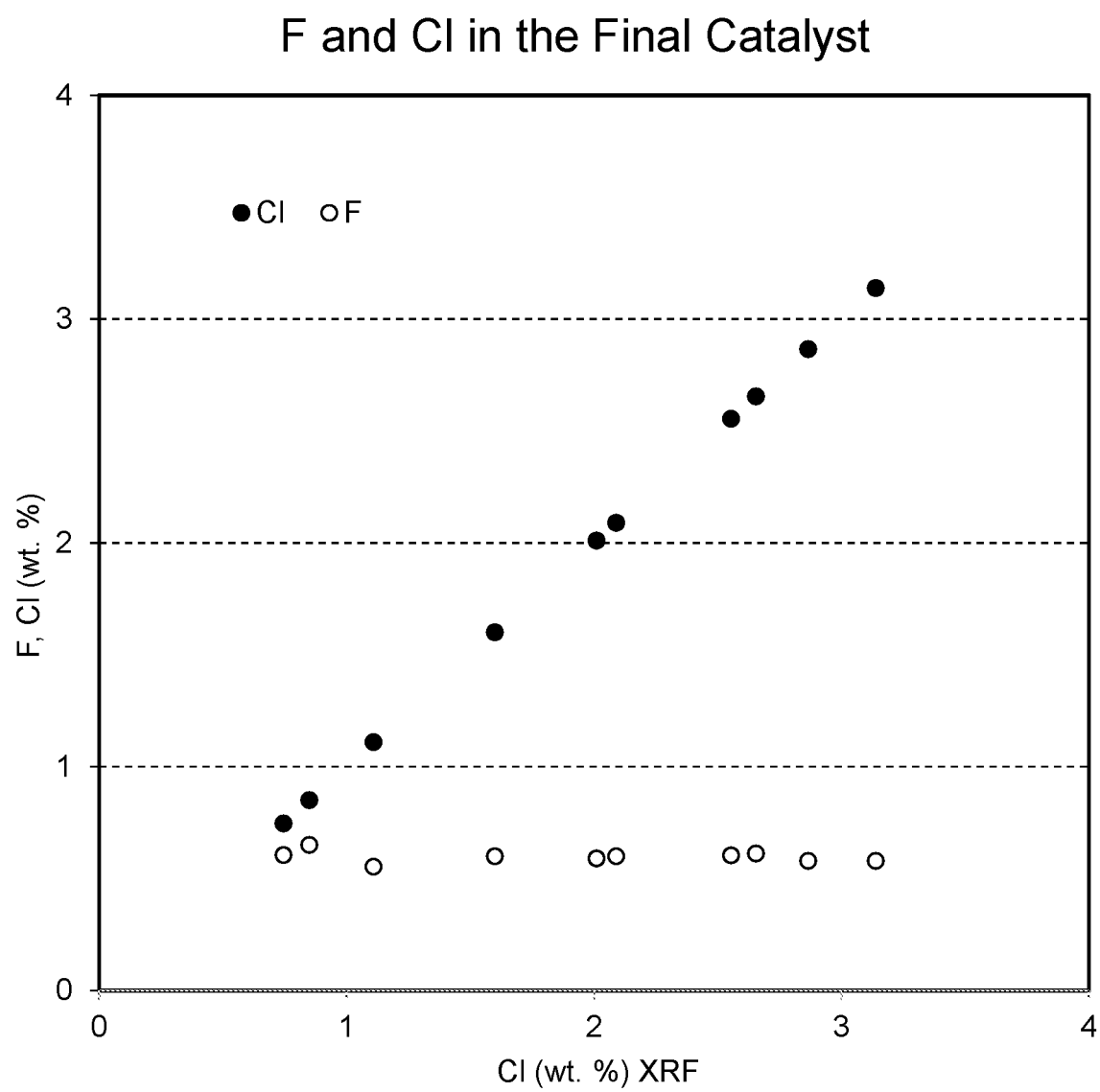
FIG. 1 presents a plot illustrating the amounts (in wt. %) of F and Cl in the supported catalysts of Example 1.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), may be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features may be envisioned. For each and every aspect and each and every feature disclosed herein, all combinations that do not detrimentally affect the designs, compositions, processes, or methods described herein are contemplated with or without explicit description of the particular combination. Additionally, unless explicitly recited otherwise, any aspect or feature disclosed herein may be combined to describe inventive designs, compositions, processes, or methods consistent with the present disclosure.

In this disclosure, while compositions and methods are often described in terms of "comprising" various components or steps, the compositions and methods may also "consist essentially of" or "consist of" the various components or steps, unless stated otherwise.

The terms "a," "an," and "the" are intended to include plural alternatives, e.g., at least one. For instance, the disclosure of "a transition metal" or "a chlorine precursor," is meant to encompass one, or mixtures or combinations of more than one, transition metal or chlorine precursor, unless otherwise specified.

Generally, groups of elements are indicated using the numbering scheme indicated in the version of the periodic table of elements published in Chemical and Engineering News, 63(5), 27, 1985. In some instances, a group of elements may be indicated using a common name assigned to the group; for example, alkali metals for Group 1 elements, transition metals for Group 3-12 elements, and halogens or halides for Group 17 elements.

For any particular compound or group disclosed herein, any name or structure (general or specific) presented is intended to encompass all conformational isomers, regioisomers, stereoisomers, and mixtures thereof that may arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane includes n-hexane, 2-methyl-pentane, 3-methyl-pentane, 2,2-dimethyl-butane, and 2,3-dimethyl-butane; and a general reference to a butyl group includes a n-butyl group, a sec-butyl group, an iso-butyl group, and a t-butyl group.

In one aspect, a chemical "group" may be defined or described according to how that group is formally derived from a reference or "parent" compound, for example, by the number of hydrogen atoms removed from the parent compound to generate the group, even if that group is not literally synthesized in such a manner. These groups may be utilized as substituents or coordinated or bonded to metal atoms. By way of example, an "alkyl group" formally may be derived by removing one hydrogen atom from an alkane. The disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

Various numerical ranges are disclosed herein. When a range of any type is disclosed or claimed herein, the intent is to disclose or claim individually each possible number that such a range could reasonably encompass, including end points of the range as well as any sub-ranges and combinations of sub-ranges encompassed therein, unless otherwise specified. As a representative example, the present application discloses that the supported catalysts may contain, in certain aspects, from about 2 wt. % to about 3.8 wt. % of chlorine, based on the total weight of the supported catalyst. By a disclosure that the chlorine content of the supported catalyst may be in a range from about 2 wt. % to about 3.8 wt. %, the intent is to recite that the chlorine content may be any amount within the range and, for example, may be equal to about 2 wt. %, about 2.2 wt. %, about 2.4 wt. %, about 2.6 wt. %, about 2.8 wt. %, about 3 wt. %, about 3.2 wt. %, about 3.4 wt. %, about 3.6 wt. %, or about 3.8 wt. %. Additionally, the chlorine content may be within any range from about 2 wt. % to about 3.8 wt. % (for example, the chlorine content may be in a range about 2.5 wt. % to about 3.3 wt. %), and this also includes any combination of ranges between about 2 wt. % and about 3.8 wt. %. Likewise, all other ranges disclosed herein should be interpreted in a manner similar to this example.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

As used herein, the term "hydrocarbon" refers to a compound containing only carbon and hydrogen atoms. Other identifiers may be utilized to indicate the presence of particular groups, if any, in the hydrocarbon (e.g., halogenated hydrocarbon indicates the presence of one or more halogen atoms replacing an equivalent number of hydrogen atoms in the hydrocarbon).

An "aromatic" compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds, e.g., benzene, toluene, and xylenes) and "heteroarenes" (heteroaromatic compounds formally derived from arenes by replacement of one or more methine (—C≡) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). As disclosed herein, the term "substituted" may be used to describe an aromatic group, arene, or heteroarene, wherein a non-hydrogen moiety formally replaces a hydrogen atom in the compound, and is intended to be non-limiting, unless specified otherwise.

As used herein, the term "alkane" refers to a saturated hydrocarbon compound. Other identifiers may be utilized to indicate the presence of particular groups, if any, in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group may be linear or branched unless otherwise specified.

A "cycloalkane" is a saturated cyclic hydrocarbon, with or without side chains, for example, cyclobutane, cyclopentane, cyclohexane, methyl cyclopentane, and methyl cyclohexane. Other identifiers may be utilized to indicate the presence of particular groups, if any, in the cycloalkane (e.g., halogenated cycloalkane indicates the presence of one or more halogen atoms replacing an equivalent number of hydrogen atoms in the cycloalkane).

As used herein, the term "convertible hydrocarbon," "convertible $C_6$ species," or "convertible $C_7$ species" refers to a hydrocarbon compound that is readily reacted to form aromatic hydrocarbons under aromatization process conditions. A "non-convertible hydrocarbon" is a highly-branched hydrocarbon that is not readily reacted to form aromatic hydrocarbons under aromatization process conditions. A "non-convertible hydrocarbon" may comprise highly-branched hydrocarbons having six or seven carbon atoms with an internal quaternary carbon, or hydrocarbons having six carbons atoms and two adjacent internal tertiary carbons, or mixtures thereof. A "convertible $C_6$ species" is a hydrocarbon containing six carbons without an internal quaternary carbon or two adjacent internal tertiary carbons, for example, n-hexane, 2-methyl-pentane, 3-methyl-pentane, cyclohexane, and methyl cyclopentane. A "convertible $C_7$ species" is a hydrocarbon containing seven carbons without an internal quaternary carbon, for example, n-heptane, 2-methyl-hexane, 3-methyl-hexane, 2,3-dimethyl-pentane, 2,4-dimethyl-pentane, methyl cyclohexane, and dimethyl cyclopentane. The highly branched hydrocarbons with six or seven carbon atoms and an internal quaternary carbon may comprise, for example, 2,2-dimethylbutane, 2,2-dimethyl-pentane, 3,3-dimethylpentane, and 2,2,3-trimethylbutane. The highly branched hydrocarbons with six carbon atoms and an adjacent internal tertiary carbon may comprise, for example, 2,3-dimethylbutane. The non-convertible highly branched hydrocarbons do not easily convert to aromatic products and instead tend to convert to light hydrocarbons under aromatization process conditions.

The term "halogen" has its usual meaning. Examples of halogens include fluorine, chlorine, bromine, and iodine.

Molar selectivities are defined as:

$$\text{Benzene selectivity}: S_{Bz} = \frac{\dot{n}_{Bz,prod}}{\dot{n}_{conv\ C6,feed} - \dot{n}_{conv\ C6,prod}} \quad \text{Eq. 1}$$

$$\text{Toluene selectivity}: S_{Tol} = \frac{\dot{n}_{Tol,prod}}{\dot{n}_{conv\ C7,feed} - \dot{n}_{conv\ C7,prod}} \quad \text{Eq. 2}$$

$$\text{Benzene+Toluene selectivity}: S_{Bz+Tol} = \quad \text{Eq. 3}$$

$$\frac{\dot{n}_{Bz,prod} + \dot{n}_{Tol,prod}}{\dot{n}_{conv\ C6,C7,feed} - \dot{n}_{conv\ C6,C7,prod}}$$

$$\text{Aromatics selectivity}: S_{arom} = \frac{\dot{n}_{Bz,prod} + \dot{n}_{Tol,prod} + \dot{n}_{C8+arom,prod}}{\dot{n}_{conv\ C6-C8+,feed} - \dot{n}_{conv\ C6-C8+,prod}} \quad \text{Eq. 4}$$

Conversion is defined as the number of moles converted per mol of "convertible" hydrocarbons fed:

$$C6\text{ conversion}: X_{C6} = \frac{\dot{n}_{conv\ C6,feed} - \dot{n}_{conv\ C6,prod}}{\dot{n}_{conv\ C6,feed}} \quad \text{Eq. 5}$$

$$C7\text{ conversion}: X_{C7} = \frac{\dot{n}_{conv\ C7,feed} - \dot{n}_{conv\ C7,prod}}{\dot{n}_{conv\ C7,feed}} \quad \text{Eq. 6}$$

$$C6 + C7\text{ conversion}: X_{C6+C7} = \quad \text{Eq. 7}$$

-continued $$\frac{\dot{n}_{conv\ C6,feed} + \dot{n}_{conv\ C7,feed} - \dot{n}_{conv\ C6,prod} - \dot{n}_{conv\ C7,prod}}{\dot{n}_{conv\ C6,feed} + \dot{n}_{conv\ C7,feed}}$$

In these equations, n indicates a molar flow rate in a continuous reactor or the number of moles in a batch reactor.

Although any methods and materials similar or equivalent to those described herein may be used in the practice or testing of the invention, the typical methods and materials are herein described.

All publications and patents mentioned herein are incorporated herein by reference for the purpose of describing and disclosing, for example, the constructs and methodologies that are described in the publications, which may be used in connection with the presently described invention.

DETAILED DESCRIPTION OF THE INVENTION

Disclosed herein are supported catalysts having a high chlorine content, methods for producing such supported catalysts, and the use of these catalysts in aromatization or reforming processes. Beneficially, as compared to traditional aromatization catalysts having a low chlorine content, the high chlorine content supported catalysts described herein have unexpectedly improved catalyst activity and stability, and lower fouling rates.

While not wishing to be bound by the following theory, it is believed that using traditional chlorine loadings that are less than that of the high chlorine content supported catalysts disclosed herein may result in inferior aromatization catalyst performance, while using chlorine loadings that are greater than that of the high chlorine content supported catalysts disclosed herein may lead to difficulties with successfully impregnating the zeolite base with the desired amounts of transition metal, chlorine, fluorine, and water. Moreover, traditional chlorine loadings were designed, in part, to maintain the non-acidic nature of the supported catalyst, with the conventional belief that increasing the acidity of the catalyst would prove detrimental to both catalyst activity and selectivity, thus making the high chlorine content supported catalysts described herein, and their improved catalytic performance, even more surprising.

Supported Catalysts

Consistent with aspects disclosed herein are supported catalysts comprising (or consisting essentially of, or consisting of) a bound zeolite base, from about 0.3 wt. % to about 3 wt. % of a transition metal, from about 1.8 wt. % to about 4 wt. % of chlorine, and from about 0.4 wt. % to about 1.5 wt. % of fluorine. These weight percentages are based on the total weight of the supported catalyst. The supported catalyst may be characterized by a peak reduction temperature on a Temperature Programmed Reduction (TPR) curve in a range from about 580° F. to about 800° F. Generally, the features of any of the catalysts disclosed herein (e.g., the bound zeolite base, the transition metal and transition metal content, the chlorine content, the fluorine content, and the characteristic of the TPR curve, among others) are independently described herein, and these features may be combined in any combination to further describe the disclosed supported catalysts.

Referring first to the bound zeolite base, any suitable bound zeolite base may be used with the high chlorine content supported catalysts described herein. Typically, the bound zeolite base may comprise an inorganic oxide, examples of which may include, but are not limited to, bound medium and/or large pore zeolites (aluminosilicates), amorphous inorganic oxides, as well as mixtures thereof. Large pore zeolites often may have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often may have average pore diameters in a range of from about 5 Å to about 7 Å. Amorphous inorganic oxides may include, but are not limited to, aluminum oxide, silicon oxide, titania, and combinations thereof.

The term "zeolite" generally refers to a particular group of hydrated, crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms may be equal to 2. The framework exhibits a negative electrovalence that typically may be balanced by the inclusion of cations within the crystal, such as metals, alkali metals, and/or hydrogen.

In some aspects, the bound zeolite base may comprise an L-type zeolite. L-type zeolite supports are a sub-group of zeolitic supports, which may contain mole ratios of oxides in accordance with the formula: $M_{2/n}OAl_2O_3xSiO_2yH_2O$. In this formula, "M" designates an exchangeable cation (one or more) such as barium, calcium, cerium, lithium, magnesium, potassium, sodium, strontium, and/or zinc, as well as non-metallic cations like hydronium and ammonium ions, which may be replaced by other exchangeable cations without causing a substantial alteration of the basic crystal structure of the L-type zeolite. The "n" in the formula represents the valence of "M"; "x" is 2 or greater; and "y" is the number of water molecules contained in the channels or interconnected voids of the zeolite.

In one aspect, the bound zeolite base may comprise a bound potassium L-type zeolite, also referred to as a K/L-zeolite, while in another aspect, the bound zeolite base may comprise a barium ion-exchanged L-zeolite. As used herein, the term "K/L-zeolite" refers to L-type zeolites in which the principal cation M incorporated in the zeolite is potassium. A K/L-zeolite may be cation-exchanged (e.g., with barium) or impregnated with a transition metal and one or more halides to produce a transition metal impregnated, halided zeolite or a K/L supported transition metal-halide zeolite catalyst.

In the bound zeolite base, the zeolite may be bound with a support matrix (or binder), and non-limiting examples of binders may include, but are not limited to, inorganic solid oxides, clays, and the like, as well as combinations thereof. The zeolite may be bound with the binder or support matrix using any method known in the art. For instance, the bound zeolite base—comprising a zeolite and a binder—may be produced by a process comprising mixing a zeolite, such as a K/L-zeolite, with a binder, such as a silica sol, then extruding the mixture to form an extrudate, followed by drying and calcining the extrudate to form a calcined base, and then washing, drying, and calcining the calcined base to form the bound zeolite base.

In some aspects, the binder may comprise alumina, silica, magnesia, boria, titania, zirconia, or a mixed oxide thereof (e.g., an aluminosilicate), or a mixture thereof, while in other aspects, the binder may comprise a montmorillonite, a kaolin, a cement, or a combination thereof. In a particular aspect contemplated herein, the binder may comprise silica, alumina, or a mixed oxide thereof; alternatively, silica; alternatively, alumina; or alternatively, silica-alumina. Accordingly, the bound zeolite base may comprise a silica-bound L-zeolite, such as a silica-bound Ba/L-zeolite, a silica-bound barium ion-exchanged L-zeolite, or a silica-bound K/L-zeolite.

While not being limited thereto, bound zeolite bases (or the supported catalysts) encompassed herein may comprise from about 3 wt. % to about 35 wt. % binder. For example, the bound zeolite base (or the supported catalyst) may comprise from about 5 wt. % to about 30 wt. %, or from about 10 wt. % to about 30 wt. % binder. These weight percentages are based on the total weight of the bound zeolite base, or based on the total weight of the supported catalyst, as the context requires.

Illustrative examples of bound zeolite bases and their use in supported catalysts are described in U.S. Pat. Nos. 5,196,631, 6,190,539, 6,406,614, 6,518,470, 6,812,180, and 7,153,801, the disclosures of which are incorporated herein by reference in their entirety.

The supported catalyst may comprise from about 0.3 wt. % to about 3 wt. % of a transition metal. For example, the supported catalyst may comprise from about 0.5 wt. % to about 2.5 wt. %, from about 0.5 wt. % to about 2 wt. %, or from about 0.7 wt. % to about 1.5 wt. % transition metal. These weight percentages are based on the total weight of the supported catalyst.

Non-limiting examples of suitable transition metals may include iron, cobalt, nickel, ruthenium, rhodium, palladium, osmium, iridium, platinum, gold, silver, copper, and the like, or a combination of two or more transition metals. In one aspect, the transition metal may comprise a Group 8-11 transition metal or a Group 8-10 transition metal (one or more), while in another aspect, the transition metal may comprise platinum (Pt). In yet another aspect, the bound zeolite base is impregnated with only one transition metal, and the transition metal is platinum.

In circumstances where the transition metal comprises platinum, the supported catalyst may comprise from about 0.3 wt. % to about 3 wt. % platinum; alternatively, from about 0.5 wt. % to about 2.5 wt. % platinum; alternatively, from about 0.5 wt. % to about 2 wt. % platinum; or alternatively, from about 0.7 wt. % to about 1.5 wt. % platinum. In a particular aspect contemplated herein, the supported catalyst may comprise platinum on a bound K/L-zeolite.

Significantly, as compared to traditional aromatization catalysts, the supported catalyst described herein has a relatively high loading of chlorine (Cl), typically ranging from about 1.8 wt. % to about 4 wt. %, based on the total weight of the supported catalyst. In one aspect, the supported catalyst may comprise from about 2 wt. % to about 3.8 wt. % chlorine. In another aspect, the supported catalyst may comprise from about 2.2 wt. % to about 3.6 wt. % chlorine. In yet another aspect, the supported catalyst may comprise from about 2.2 wt. % to about 3.4 wt. % chlorine. In still another aspect, the supported catalyst may comprise from about 2 wt. % to about 3.3 wt. % chlorine, or from about 2.5 wt. % to about 3.3 wt. % chlorine. Unexpectedly, it was found that high loadings of chlorine in the supported catalyst may provide improved catalyst activity and stability, and lower fouling rates.

The supported catalyst also comprises fluorine (F), which often ranges from about 0.4 wt. % to about 1.5 wt. %, or from about 0.5 wt. % to about 1.5 wt. %, based on the total weight of the supported catalyst. For instance, the supported catalyst may comprise from about 0.5 wt. % to about 1.3 wt. % fluorine, from about 0.5 wt. % to about 1.1 wt. % fluorine, or from about 0.6 wt. % to about 0.9 wt. % fluorine.

While not being limited thereto, the high chlorine content supported catalyst may be characterized by a weight ratio of chlorine:fluorine that often falls within a range from about 1.5:1 to about 8:1, or from about 2:1 to about 6:1. In some aspects, the weight ratio of chlorine:fluorine may range from about 2:1 to about 5:1, while in other aspects, the weight ratio may range from about 3:1 to about 4.5:1.

Unexpectedly, the high chlorine content supported catalysts described herein may have Temperature Programmed Reduction (TPR) curves that are distinctly different from traditional low chlorine content supported catalysts (i.e., having from 0.3 wt. % to 1.5 wt. % Cl). In one aspect, for instance, the high chlorine content supported catalysts disclosed herein may be characterized by a peak temperature on a TPR curve in a range from about 580° F. to about 800° F. In another aspect, the peak temperature on the TPR curve may fall within a range from about 580° F. to about 750° F., from about 600° F. to about 730° F., from about 600° F. to about 720° F., or from about 630° F. to about 690° F. The peak temperature on the TPR curve is the temperature of the highest peak on the TPR curve. As shown in the examples that follow, the peak temperatures for traditional low chlorine content supported catalysts are much lower.

A "traditional low chlorine content supported catalyst" generally encompasses aromatization catalysts, as described herein, that contain any amount of Cl in the range from 0.3 wt. % to 1.5 wt. % Cl, based on the total weight of the supported catalyst. Thus, a traditional low chlorine content supported catalyst may include a supported catalyst having any Cl content within the 0.3 wt. % to 1.5 wt. % range, such as from 0.3 wt. % to 1.2 wt. % Cl, or from 0.5 wt. % to 1.1 wt. % Cl. Additionally, the traditional low chlorine content supported catalyst may have a Cl content of about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, or about 1.4 wt. %.

In another aspect, for instance, the high chlorine content supported catalysts disclosed herein may be characterized by a peak temperature on a TPR curve that is at least 100° F. higher than the peak TPR temperature for a traditional low chlorine content supported catalyst. In another aspect, the peak temperature on the TPR curve may be at least about 150° F. higher, at least about 200° F. higher, from about 100° F. to about 400° F. higher, from about 120° F. to about 300° F. higher, or from about 100° F. to about 250° F. higher.

In addition, the high chlorine content supported catalysts disclosed herein may be characterized by a TPR curve having a lower temperature peak and a higher temperature peak (i.e., two peaks), and the higher temperature peak is greater in height than the lower temperature peak. As shown in the examples that follow, the opposite is true for low chlorine content supported catalysts—i.e., the lower temperature peak is greater in height than the higher temperature peak.

Moreover, the high chlorine content supported catalysts disclosed herein may have a total nitrogen (N) content that is greater than that of low chlorine content supported catalysts (i.e., having from 0.3 wt. % to 1.5 wt. % Cl), when compared under the same catalyst preparation conditions. In some instances, the total nitrogen content of the high chlorine content supported catalyst may be at least about 50% greater, at least about 100% greater, or at least about 200% greater, and often up to 500-1000% greater, than that of the low chlorine content supported catalyst.

In some aspects, the supported catalyst comprises nitrogen (N), which often ranges from about 0.4 wt. % to about 1.6 wt. %, based on the total weight of the supported catalyst. For instance, the supported catalyst may comprise from about 0.5 wt. % to about 1.4 wt. % nitrogen, from about 0.6 wt. % to about 1.3 wt. % nitrogen, or from about 0.7 wt. % to about 1.2 wt. % nitrogen.

Furthermore, the performance of the high chlorine content supported catalysts disclosed herein in aromatization reactions is improved. Surprisingly, these supported catalysts have higher catalyst activity and stability, as quantified by the $T_{SOR}$ (start of run temperature), $T_{EOR}$ (end of run temperature), and FR (fouling rate) metrics discussed in greater detail in the examples that follow. Generally, the high chlorine content supported catalysts described herein may have a lower $T_{SOR}$, a lower $T_{EOR}$, and/or a lower FR than that of a low chlorine content supported catalyst (i.e., having from 0.3 wt. % to 1.5 wt. % chlorine), when compared under the same catalyst preparation and aromatization reaction conditions. Thus, the comparison is for supported catalysts having the same platinum, fluorine, and other compositional attributes (with the exception of chlorine content), and prepared in the same manner, and tested under the same aromatization reaction conditions (see Example 3 below).

The high chlorine content supported catalysts may be characterized by a $T_{SOR}$ (start of run temperature), as described herein, which often may fall within a range from about 915° F. to about 935° F., or from about 915° F. to about 930° F. Additionally or alternatively, these supported catalysts may be characterized by a $T_{EOR}$ (end of run temperature), as described herein, which often may fall within a range from about 920° F. to about 940° F., or from about 920° F. to about 930° F. Additionally or alternatively, these supported catalysts may be characterized by a FR (fouling rate), as described herein, which often may be less than about 0.12° F./min, or less than about 0.1° F./min.

In contrast to these improvements, and unexpectedly, the high chlorine content supported catalysts may have surface areas and platinum dispersions that are comparable to those of low chlorine content supported catalysts (i.e., having from 0.3 wt. % to 1.5 wt. % chlorine), when compared under the same catalyst preparation conditions. For instance, the high chlorine content supported catalysts may have surface areas and platinum dispersions that are substantially the same as those of low chlorine content supported catalysts, when compared under the same catalyst preparation conditions. In these circumstances, "substantially" the same means within +/−20%, and more typically, within +/−15%, or within +/−10%.

In addition, the high chlorine content supported catalysts may be characterized by an aromatics selectivity (or a benzene+toluene selectivity) that is substantially the same as that of a low chlorine content supported catalyst (having from 0.3 wt. % to 1.5 wt. % chlorine), when compared under the same catalyst preparation and aromatization reaction conditions. In these circumstances, "substantially" the same means within +/−10%, and more typically, within +/−6%, or within +/−4%.

Methods for Producing Supported Catalysts

Various methods for producing supported catalysts, such as supported aromatization catalysts, are disclosed and described. One such method for producing a supported catalyst may comprise (or consist essentially of, or consist of) (a) impregnating a bound zeolite base with a transition metal precursor, a chlorine precursor, and a fluorine precursor to form an impregnated zeolite base; and (b) drying and then calcining the impregnated zeolite base to produce the supported catalyst. The supported catalyst may comprise, based on the total weight of the supported catalyst, from about 0.3 wt. % to about 3 wt. % of a transition metal, from about 1.8 wt. % to about 4 wt. % of chlorine, and from about 0.4 wt. % to about 1.5 wt. % of fluorine. Further, the supported catalyst may be characterized by a peak reduction temperature on a Temperature Programmed Reduction (TPR) curve in a range from about 580° F. to about 800° F.

Generally, the features of any of the methods disclosed herein (e.g., the bound zeolite base, the transition metal precursor, the transition metal and transition metal content, the chlorine precursor, the chlorine content, the fluorine precursor, the fluorine content, the characteristics of the TPR curve, the conditions under which the impregnation step is conducted, the conditions under which the drying and calcining are conducted, among others) are independently described herein, and these features may be combined in any combination to further describe the disclosed supported methods. Moreover, other process steps may be conducted before, during, and/or after any of the steps listed in the disclosed methods, unless stated otherwise. Additionally, supported catalysts (such as supported aromatization catalysts) produced in accordance with any of the disclosed methods/processes are within the scope of this disclosure and are encompassed herein.

Referring now to step (a) of the method for producing a supported catalyst (often referred to as the impregnation step), the bound zeolite base may be impregnated with a transition metal precursor, a chlorine precursor, and a fluorine precursor to form an impregnated zeolite base. The bound zeolite base in step (a) may be produced by any technique known to those skilled in the art. For instance, the bound zeolite base—comprising a zeolite and a binder—may be produced by a process comprising mixing or combining a zeolite with a binder to form a mixture, then extruding the mixture to form an extrudate, followed by drying and calcining the extrudate to form a calcined base, and then washing, drying, and calcining the calcined base to form the bound zeolite base.

The transition metal precursor, chlorine precursor, and fluorine precursor in the impregnation step encompass any compounds that may deposit the transition metal, chlorine, and/or fluorine in or on the bound zeolite base, thereby forming the impregnated zeolite base. This description is meant to encompass (1) compounds that serve as precursor for only one material—for example, ammonium chloride may be a chlorine precursor for chlorine—and (2) compounds that serve as precursor for more than one material—for example, platinum(II) chloride may be both a transition metal precursor and a chlorine precursor for platinum and chlorine, while a chlorofluorocarbon compound may be both a chlorine precursor and a fluorine precursor for chlorine and fluorine.

Illustrative and non-limiting examples of transition metal precursors that are suitable for use in impregnating the bound zeolite base with platinum include, but are not limited to, tetraamineplatinum(II) chloride, tetraamineplatinum(II) nitrate, platinum(II) acetylacetonate, platinum(II) chloride, ammonium tetrachloroplatinate(II), chloroplatinic acid, platinum (II) nitrate, and the like, as well as mixtures or combinations thereof. Illustrative and non-limiting examples of chlorine precursors include hydrochloric acid, carbon tetrachloride, tetrachloroethylene, chlorobenzene, methyl chloride, methylene chloride, chloroform, allyl chloride, trichloroethylene, a chloramine, a chlorine oxide, a chlorine acid, chlorine dioxide, dichlorine monoxide, dichlorine heptoxide, chloric acid, perchloric acid, ammonium chloride, tetramethylammonium chloride, tetraethylammonium chloride, tetrapropylammonium chloride, tetrabutylammonium chloride, methyltriethylammonium chloride, and the like, as well as combinations thereof. Illustrative and non-limiting examples of fluorine precursors include hydrofluoric acid, 2,2,2-trifluoroethanol, tetrafluoroethylene, carbon tetrafluoride, carbon trifluoride, fluoromethane, heptafluoropropane, decafluorobutane, hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, ammonium fluoride, tetramethylammonium fluoride, tetraethyl ammonium fluoride, tetrapropylammonium fluoride, tetrabutylammonium fluoride, methyltriethylammonium fluoride, and the like, as well as combinations thereof.

Any suitable method or technique known to those of skill in the art that results in adequate dispersion of the transition metal on the supported catalyst may be used in the impregnation step. One such method involves mixing the bound zeolite base with any suitable transition metal precursor, where the transition metal precursor may be present in a solution of any suitable solvent, such as water. Likewise, for the halogens, the impregnation step may comprise mixing the bound zeolite base with any suitable chlorine precursor and/or fluorine precursor, and in any order or sequence. For instance, the bound zeolite base may be mixed with a solution of the chlorine precursor, a solution of the fluorine precursor, or a solution of both the chlorine precursor and the fluorine precursor in a suitable solvent. In one aspect, the bound zeolite base may be mixed with a combination of the transition metal precursor, the chlorine precursor, and the fluorine precursor (i.e., all together), such as may be accomplished by mixing the bound zeolite base with an aqueous solution comprising the transition metal precursor, the chlorine precursor, and the fluorine precursor. An incipient wetness technique may be used. In another aspect, the combining of the transition metal precursor, the chlorine precursor, and the fluorine precursor with the bound zeolite base may be done sequentially, or in any order or combination.

Yet, in other aspects, the bound zeolite base may be impregnated with chlorine and/or fluorine in the vapor phase. For instance, the bound zeolite base may be contacted with a stream comprising a chlorine precursor and/or a fluorine precursor. Suitable chlorine precursors and fluorine precursors may include those listed hereinabove, as well as chlorine gas ($Cl_2$) and fluorine gas ($F_2$).

Referring now to step (b), the impregnated zeolite base may be dried and then calcined to produce the supported catalyst. Any suitable temperatures, pressures, time periods, and atmospheres may be used in the drying and calcining steps.

In one aspect, the drying step may comprise contacting the impregnated zeolite base with a drying gas stream comprising (or consisting essentially, or consisting of) an inert gas (e.g., nitrogen), oxygen, air, or any mixture or combination thereof; alternatively, nitrogen; alternatively, helium; alternatively, neon; alternatively, argon; alternatively, oxygen; or alternatively, air. While not being limited thereto, the drying step generally may be conducted at a drying temperature in a range from about 50° C. to about 200° C.; alternatively, from about 100° C. to about 200° C.; alternatively, from about 85° C. to about 175° C.; or alternatively, from about 80° C. to about 150° C. In these and other aspects, these temperature ranges also are meant to encompass circumstances where the drying step is conducted at a series of different temperatures, instead of at a single fixed temperature, falling within the respective ranges. In some aspects, the drying step may be performed at atmospheric pressure, or at any suitable sub-atmospheric pressure, such as less than about 150 Torr, less than about 125 Torr, less than about 100 Torr, or less than about 50 Torr.

The duration of the drying step is not limited to any particular period of time. Typically, the drying step may be conducted in a time period ranging from as little as 30 minutes to as long as 8 hours (or more), but more typically, the drying step may be conducted in a time period that may be in a range from about 1 hour to about 8 hours, such as, for example, from about 1 hour to about 7 hours, from about 1 hour to about 6 hours, from about 2 hours to about 7 hours, or from about 2 hours to about 6 hours.

The calcining step may be conducted at a variety of temperatures and time periods. Typical peak calcining temperatures often fall within a range from about 200° C. to about 600° C., such as from about 215° C. to about 500° C., from about 230° C. to about 450° C., or from about 230° C. to about 350° C. In these and other aspects, these temperature ranges also are meant to encompass circumstances where the calcination step is conducted at a series of different temperatures (e.g., an initial calcination temperature, a peak calcination temperature), instead of at a single fixed temperature, falling within the respective ranges. For instance, the calcination step may start at an initial temperature which is the same as the drying temperature in the drying step. Subsequently, the temperature of the calcination may be increased over time to a peak calcining temperature, for example, in a range from about 230° C. to about 350° C.

The duration of the calcining step is not limited to any particular period of time. Hence, the calcining step may be conducted, for example, in a time period ranging from as little as 30-45 minutes to as long as 10-12 hours, or more. The appropriate calcining time may depend upon, for example, the initial/peak calcining temperature and the conditions of the drying step, among other variables. Generally, however, the calcining step may be conducted in a time period that may be in a range from about 45 minutes to about 12 hours, such as, for example, from about 1 hour to about 12 hours, from about 1 hour to about 10 hours, from about 1 hour to about 5 hours, or from about 1 hour to about 3 hours.

The calcining step may be conducted in a calcining gas stream that comprises (or consists essentially of, or consists of) an inert gas (e.g., nitrogen), oxygen, air, or any mixture or combination thereof. In some aspects, the calcining gas stream may comprise air, while in other aspects, the calcining gas stream may comprise a mixture of air and nitrogen. Yet, in certain aspects, the calcining gas stream may be an inert gas, such as nitrogen and/or argon.

The methods for preparing a supported catalyst disclosed herein may further comprise a reducing step after step (b), i.e., after drying and calcining the impregnated zeolite base to produce the supported catalyst. This reducing step may comprise contacting the supported catalyst with a reducing gas stream comprising hydrogen to produce a reduced (or activated) supported catalyst. Often, the reducing gas stream comprises molecular hydrogen, either alone or with an inert gas, such as helium, neon, argon, nitrogen, and the like, and this includes combinations of two or more of these inert gasses. In certain aspects, the reducing gas stream may comprise (or consist essentially of, or consist of) molecular hydrogen and nitrogen. Moreover, molecular hydrogen may be the major component of the reducing gas stream (greater than 50 mol %), while in other aspects, molecular hydrogen may be a minor component (between 5-35 mol %, or between 1-6 mol %). In another aspect, the reducing gas stream may comprise (or consist essentially of, or consist of) molecular hydrogen and hydrocarbons.

The reducing step may be conducted at a variety of temperatures and time periods. For instance, the reducing step may be conducted at a reducing temperature in a range from about 100° C. to about 700° C.; alternatively, from about 200° C. to about 600° C.; alternatively, from about 200° C. to about 575° C.; alternatively, from about 350° C. to about 575° C.; alternatively, from about 400° C. to about 550° C.; or alternatively, from about 450° C. to about 550° C. In these and other aspects, these temperature ranges also are meant to encompass circumstances where the reducing step is conducted at a series of different temperatures, instead of at a single fixed temperature, falling within the respective ranges.

The duration of the reducing step is not limited to any particular period of time. Hence, the reducing step may be conducted, for example, in a time period ranging from as little as 1 hour to as long as 48-72 hours, or more. For example, the reducing step may be conducted in a time period that may be in a range from about 1 hour to about 48 hours, from about 3 hours to about 36 hours, from about 5 hours to about 36 hours, from about 2 hours to about 30 hours, or from about 10 hours to about 30 hours.

In one aspect, the reducing step may be performed ex-situ. In this aspect, the high chlorine content supported catalyst is converted to a reduced (or activated) supported catalyst according to the procedures described above. This reduction may occur at the catalyst manufacturing site or another site. The reduced (or activated) supported catalyst may then be packaged under air or under an inert gas and is then stored prior to being loaded into the aromatization reactor and used in the aromatization reactor system. Prior to use, a reduction step may be performed to reduce any supported catalyst that became oxidized after the first reduction, for example during storage, transport and loading. This second reduction may require the same or less time than the in-situ reduction described below.

In another aspect, the reducing step may be performed in-situ. In this aspect, the high chlorine content supported catalyst is packaged after the calcining step. The high chlorine content supported catalyst may be stored for an extended period of time prior to loading into the aromatization reactor. After loading, the high chlorine content supported catalyst is then converted to a reduced (or activated) supported catalyst according to the procedures described above.

Unexpectedly, despite the high chlorine content of the supported catalysts disclosed herein, the reduced (or activated) supported catalyst may have significantly less chlorine present after the reducing step. For instance, the reduced (or activated) supported catalyst may comprise from about 0.2 wt. % to about 1.3 wt. % chlorine, from about 0.2 wt. % to about 0.8 wt. % chlorine, or from about 0.3 wt. % to about 1 wt. % chlorine. These weight percentages are based on the total weight of the reduced (or activated) supported catalyst.

Reforming Processes with Aromatization Catalysts

Also encompassed herein are various processes for reforming hydrocarbons. One such reforming process may comprise (or consist essentially of, or consist of) contacting a hydrocarbon feed with a supported aromatization catalyst under reforming conditions in a reactor system to produce an aromatic product. The supported aromatization catalyst used in the reforming process may be any supported catalyst disclosed herein (i.e., any high chlorine content supported catalyst disclosed herein) and/or may be produced by any method for producing a supported catalyst disclosed herein.

The reactor systems for reforming and the respective reforming conditions are well known to those of skill in the art and are described, for example, in U.S. Pat. Nos. 4,456,527, 5,389,235, 5,401,386, 5,401,365, 6,207,042, and 7,932,425, the disclosures of which are incorporated herein by reference in their entirety.

Likewise, typical hydrocarbon feeds are disclosed in these references. Often, the hydrocarbon feed may be a naphtha stream or light naphtha stream. In certain aspects, the hydrocarbon feed may comprise non-aromatic hydrocarbons, for example, the hydrocarbon feed may comprise $C_6$-$C_9$ alkanes and/or cycloalkanes, or $C_6$-$C_8$ alkanes and/or cycloalkanes (e.g., hexane, heptane, cyclohexane), and the like.

As described herein, and unexpectedly, the high chlorine content supported catalysts herein may have improved catalyst activity and stability, and reduced fouling rates in aromatization or reforming reactions, as compared to low chlorine content supported catalysts (i.e., having from 0.3 wt. % to 1.5 wt. % Cl).

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Weight percentages of Pt, Cl, F, and N were determined using X-ray fluorescence (XRF), and are based on the total weight of the supported catalyst, unless stated otherwise. Surface areas were determined using the BET method, and platinum dispersions were determined by CO Chemisorption.

Supported catalysts were tested for their performance in aromatization reactions using the following general procedure, unless noted otherwise. The supported aromatization catalysts were ground and sieved to about 25-45 mesh (US), and 1 cc of the sieved supported catalyst was placed in a ⅜-inch OD stainless steel reactor vessel in a temperature controlled furnace. After reducing the supported catalyst under flowing molecular hydrogen, a feed stream of aliphatic hydrocarbons and molecular hydrogen was introduced to the reactor vessel at a pressure of 100 psig, a hydrogen:hydrocarbon molar ratio of 1.3:1, and a liquid hourly space velocity (LHSV) of 12 $hr^{-1}$. The aliphatic hydrocarbon feed contained approximately 0.61 mole fraction of convertible $C_6$ species and 0.21 mole fraction of convertible $C_7$ species. The balance was aromatics, $C_8$+, and non-convertible hydrocarbon.

The reactor temperature was then adjusted to maintain a target conversion of 63 wt. % aromatics in the $C_5^+$ fraction of the reactor effluent as determined gas chromatography. The amounts of the numerous feedstock components and product components, including benzene and toluene present, also were recorded for selectivity calculations.

The temperature at the start of run ($T_{SOR}$) and the fouling rate (abbreviated FR, units of ° F./hr.) of a supported catalyst sample was determined by plotting the temperature (yield-adjusted catalyst temperature) required to maintain a total yield of aromatics (such as benzene and toluene) at 63 wt. % over time at the standard test conditions provided above. As used herein, the term "yield-adjusted temperature" refers to the catalyst bed temperature in a lab-scale reactor system which has been adjusted to account for samples taken when the reactor effluent does not contain 63 wt. % aromatics in the $C_5^+$ fraction of the reactor effluent. The adjustment factor (for example, in units of ° F./wt. %) was determined by prior experiments with similar catalysts. A linear regression analysis of the temperatures collected between 15 and 40 hours results in the formula, $T_{adj}=FR*t+T_{SOR}$, where $T_{adj}$ is the yield-adjusted temperature, FR is the fouling rate, t is time, and $T_{SOR}$ is the Start of Run temperature (temperature needed to achieve 63 wt. % aromatics yield at a hypothetical time zero). The total time on stream was 40 hours, and the End of Run temperature (abbreviated $T_{EOR}$) at 40 hours also was determined; $T_{EOR}$ is the temperature needed to achieve 63 wt. % aromatics yield at the end of the 40-hour run. Initial low conversion and catalyst break-in conditions were the primary reasons that the temperatures prior to 15 hours were not included in the determination of $T_{SOR}$ and FR.

Temperature-programmed reduction (TPR) is a method of examining the reducibility of catalytically active materials, in these examples with hydrogen, as a function of the temperature. For the TPR test, the calcined catalyst was ground and sieved to 25-45 mesh (US) and placed in a sample vessel, which can be, for example, a simple U-tube. This sample vessel was then positioned in an oven equipped with temperature regulation and a thermocouple to record the temperature of the catalyst bed. The sample vessel was first purged with an inert gas (for example, argon or nitrogen). After a few minutes, 10% by volume of hydrogen was introduced into the inert gas stream by means of a flow regulator at a total gas flow rate of 50 cc/min. The sample vessel was flushed with the measurement gas at room temperature before commencement of the measurement. The sample vessel was then heated in the oven at a rate of 10° C./min. The effluent from the sample vessel was passed to a thermal conductivity detector for determination of hydrogen uptake as a function of temperature.

Example 1

A standard bound KL-zeolite base consisting of approximately 17 wt. % silica binder was used as the starting material for Example 1. The bound zeolite base was impregnated with Pt, Cl, and F via incipient wetness techniques by contacting the bound zeolite base with an aqueous solution containing platinum tetraammonium chloride ($Pt(NH_3)_4Cl_2.xH_2O$), ammonium chloride, and ammonium fluoride. Then, the impregnated base was dried at 95° C., and calcined at 900° F. to form the supported aromatization catalysts.

Figure 2:
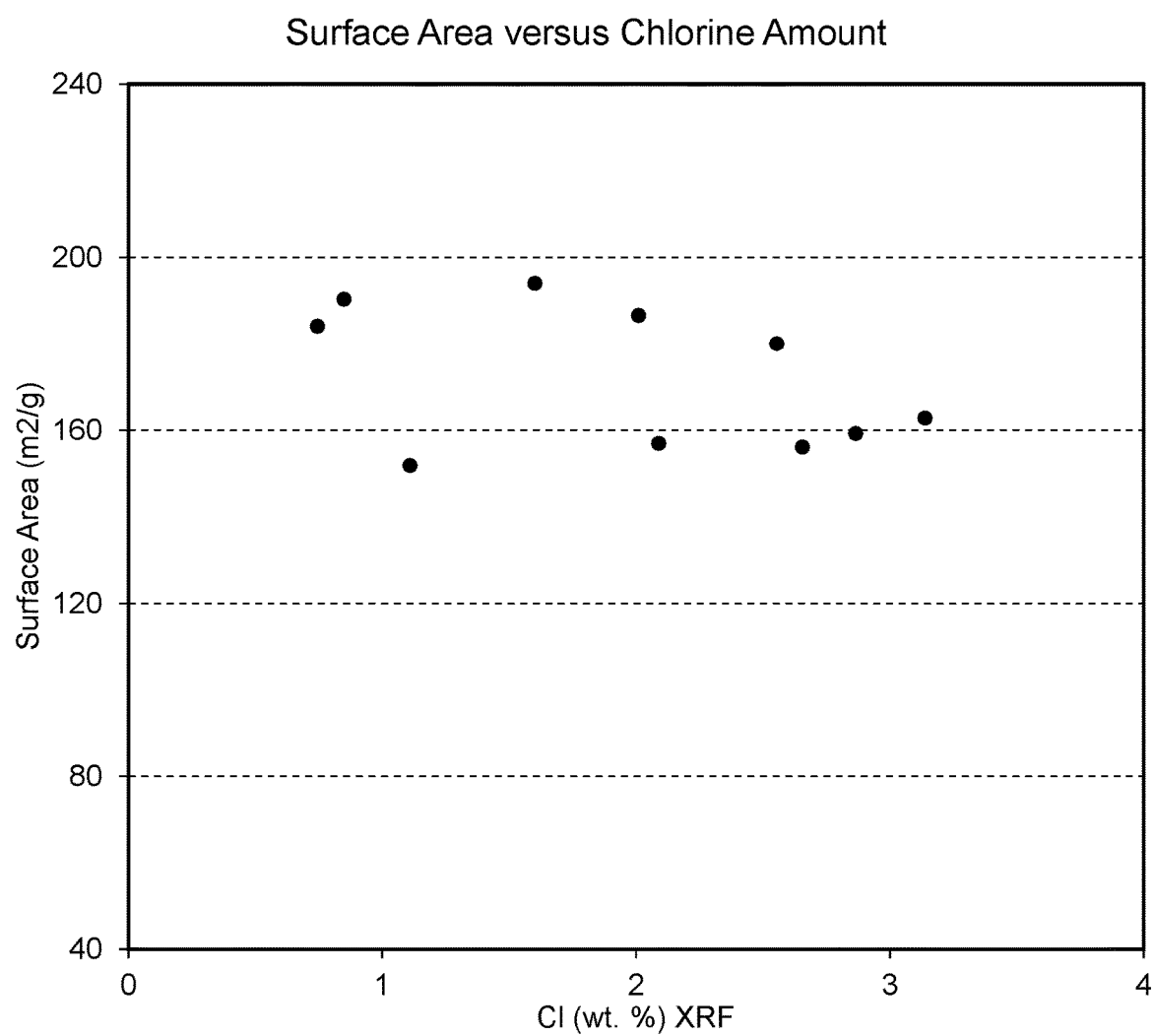
FIG. 2 presents a plot of the surface area of the supported catalysts of Example 1 versus the amount (in wt. %) of Cl in the supported catalysts.
Figure 3:
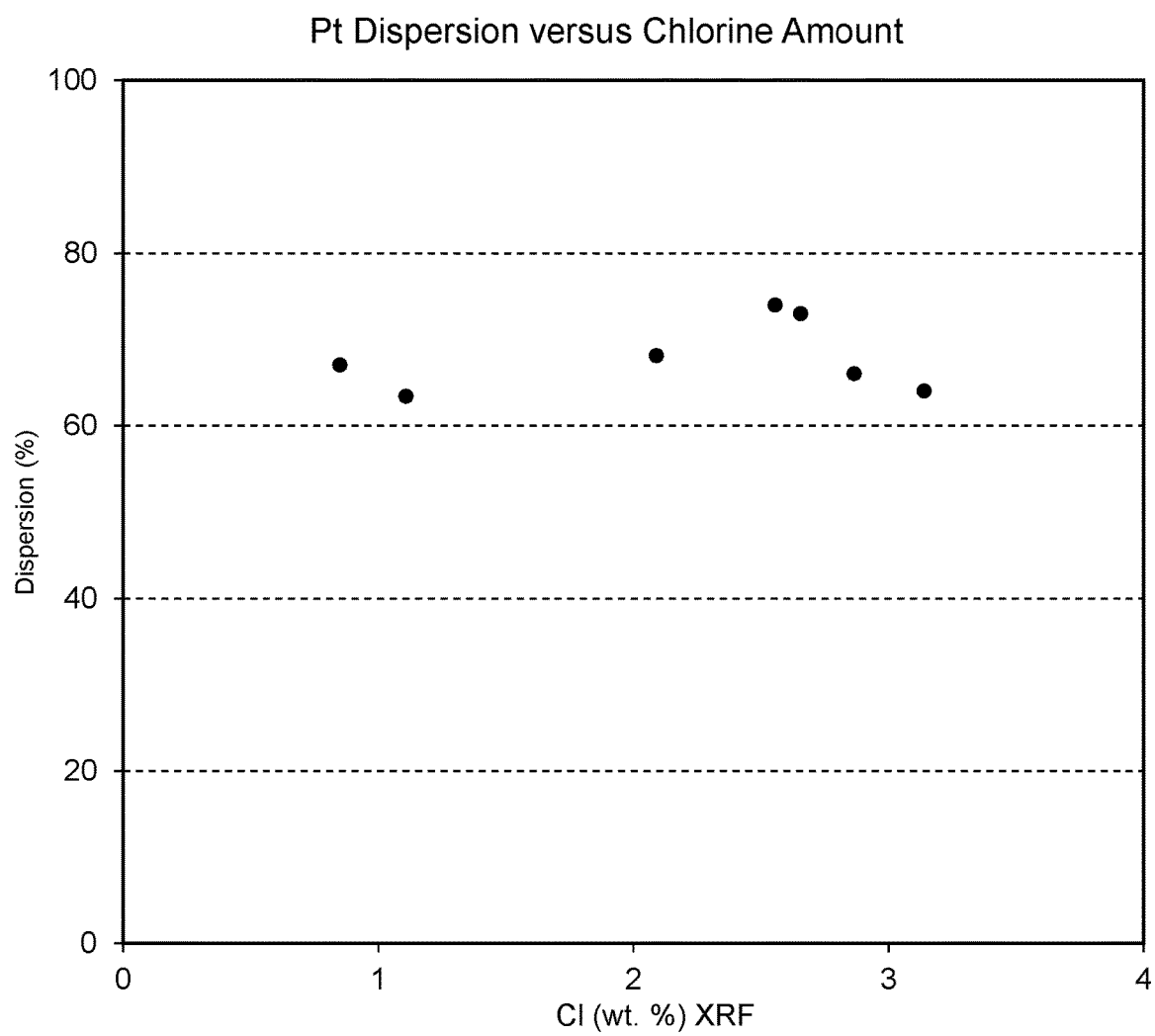
FIG. 3 presents a plot of the platinum dispersion of the supported catalysts of Example 1 versus the amount (in wt. %) of Cl in the supported catalysts.
Figure 4:
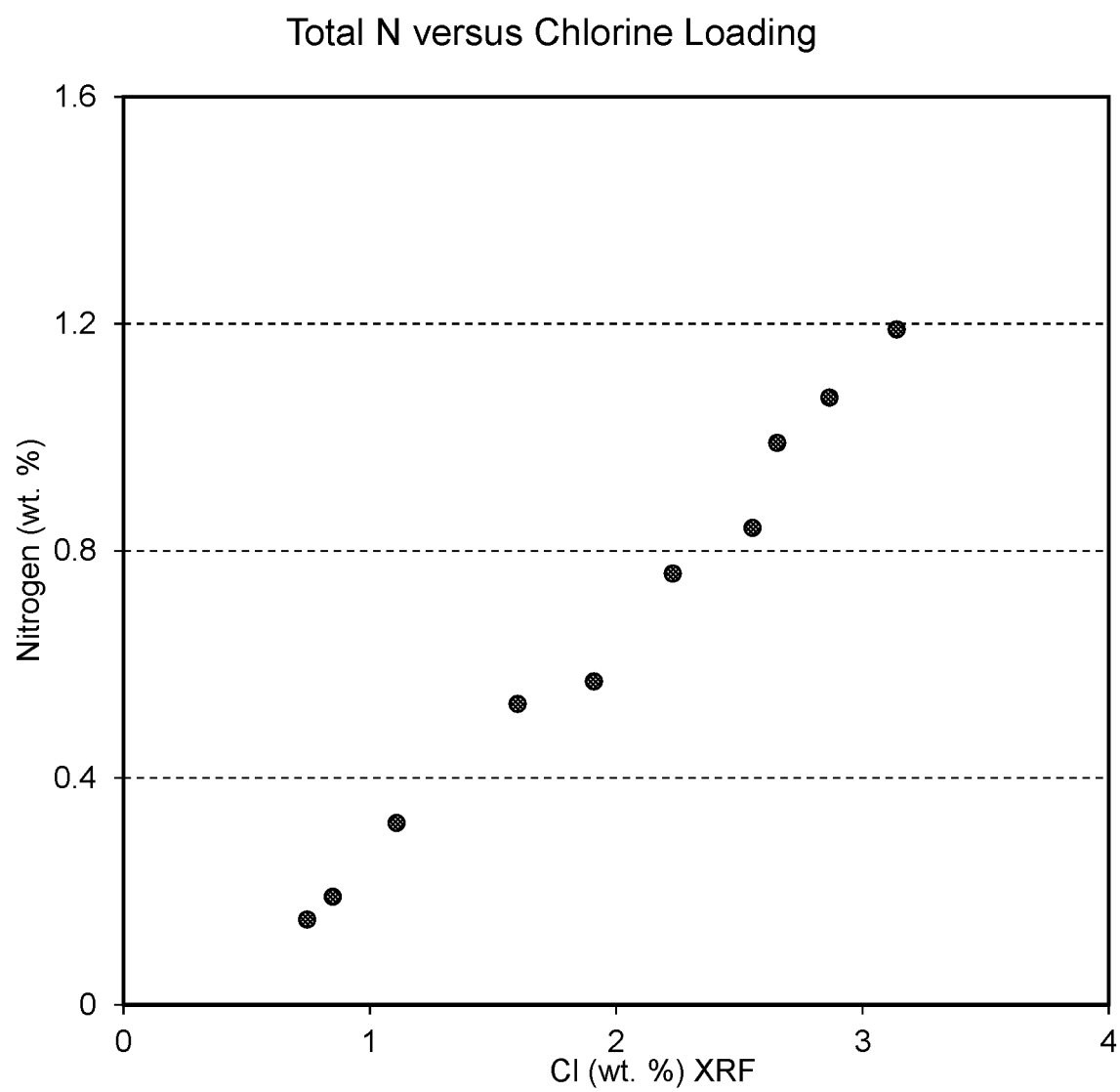
FIG. 4 presents a plot illustrating the amounts (in wt. %) of N and Cl in the supported catalysts of Example 1.

In Example 1, supported catalysts containing approximately 1 wt. % Pt, 0.6 wt. % F, and a range of Cl contents were produced. FIG. 1 illustrates the F and Cl contents of these supported catalysts, with the amount of Cl ranging from less than 1 wt. % to over 3 wt. %. Despite this large range of Cl contents, the surface areas of the supported catalysts were substantially constant, as shown in FIG. 2, and the platinum dispersions in the supported catalysts were substantially constant, as shown in FIG. 3. In contrast, FIG. 4 demonstrates that the N content of the supported catalyst increased linearly with the Cl content of the supported catalyst.

Example 2

In Example 2, supported catalysts were produced as described in Example 1, and the range of Cl contents was from 0.7 wt. % to 3.1 wt. %. These supported catalysts were compared to two standard supported catalysts: a Large-Scale Control (having 0.98 wt. % Pt, 0.85 wt. % Cl, and 0.71 wt. % F) and a Laboratory Control (having 1.01 wt. % Pt, 0.87 wt. % Cl, and 0.61 wt. % F). The Large-Scale Control and Laboratory Control are nearly identical supported catalysts, with the Large-Scale Control being a historical control catalyst produced on large-scale equipment typical of a catalyst manufacturer, and the Laboratory Control being a control catalyst made in the laboratory at the same time and using the same equipment as the experimental catalysts.

Figure 5:
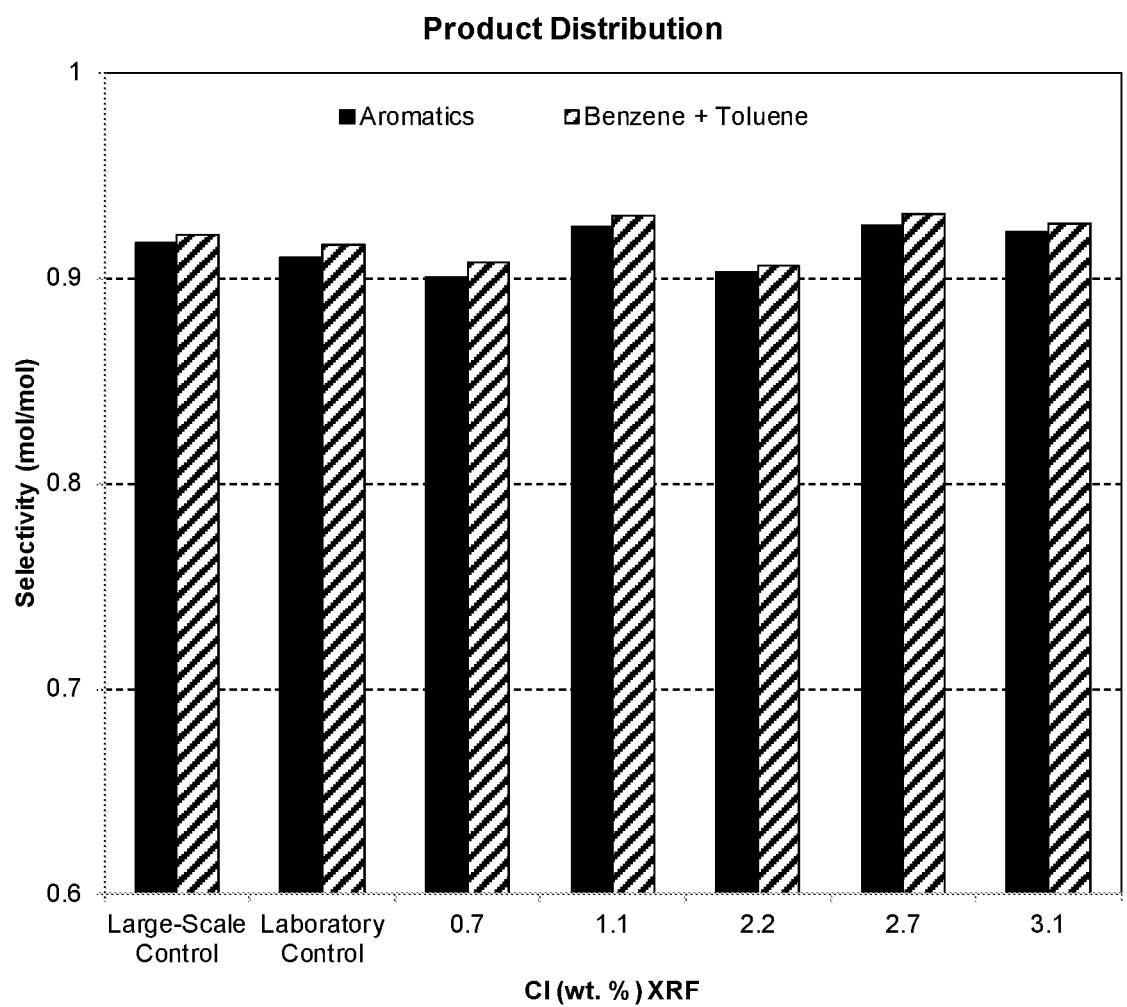
FIG. 5 presents a plot of the molar aromatics selectivity and the molar benzene+toluene selectivity for the supported catalysts of Example 2.

Using the 40-hour test procedure described above, the selectivity to aromatics and selectivity for benzene+toluene were determined for each supported catalyst. FIG. 5 compares the average aromatics selectivity and the average benzene+toluene selectivity for these supported catalysts. As shown in FIG. 5, the selectivity performance of the supported catalysts with 0.7 wt. % to 3.1 wt. % Cl was comparable to the standard catalysts, and the amount of Cl (high versus low) did not significantly impact the selectivity performance of the supported catalysts.

Example 3

In Example 3, supported catalysts were produced as described in Example 1, and the Cl contents were 0.75 wt. %, 1.1 wt. %, 2.2 wt. %, 2.7 wt. %, and 3.1 wt. %. These supported catalysts were compared to the two standard aromatization catalysts: the Large-Scale Control and the Laboratory Control.

Figure 6:
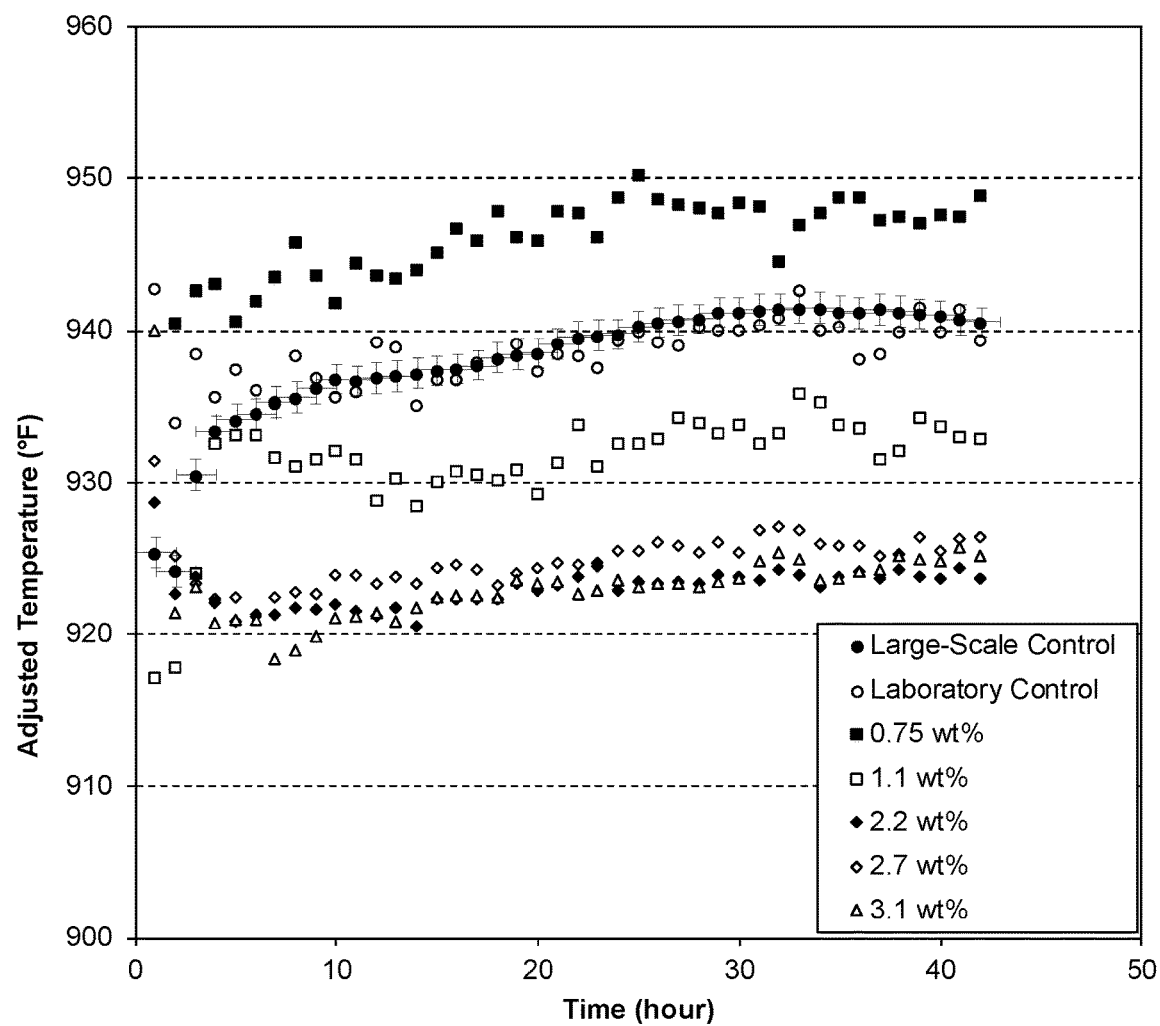
FIG. 6 presents a plot of the yield-adjusted temperature versus reaction time for the supported catalysts of Example 3.

FIG. 6 compares the yield-adjusted temperature versus the reaction time for each supported catalyst, using the 40-hour test procedure described above. Table I summarizes the relevant catalyst performance metrics from FIG. 6. As shown in the table and figure, the high chlorine content supported catalysts (2.2 to 3.1 wt. %), unexpectedly, had the best performance of all of the catalysts: the highest catalyst activities (lowest $T_{SOR}$ and $T_{EOR}$) and the lowest fouling rates. Interestingly, these beneficial results were achieved without significant changes in catalyst surface area, platinum dispersion, or catalyst selectivity (see Example 1 and Example 2).

TABLE I

Example 3-Catalyst performance summary.

| Chlorine (wt. %) | $T_{SOR}$ (° F.) | $T_{EOR}$ (° F.) | Fouling Rate (° F./hr.) |
|---|---|---|---|
| 0.85 Large-Scale Control | 936 | 941 | 0.14 |
| 0.87 Experimental Control | 936 | 941 | 0.12 |
| 0.75 | 946 | 950 | 0.05 |
| 1.1 | 929 | 934 | 0.13 |
| 2.2 | 922 | 925 | 0.05 |
| 2.7 | 923 | 926 | 0.08 |
| 3.1 | 920 | 925 | 0.10 |

Example 4

Figure 7:
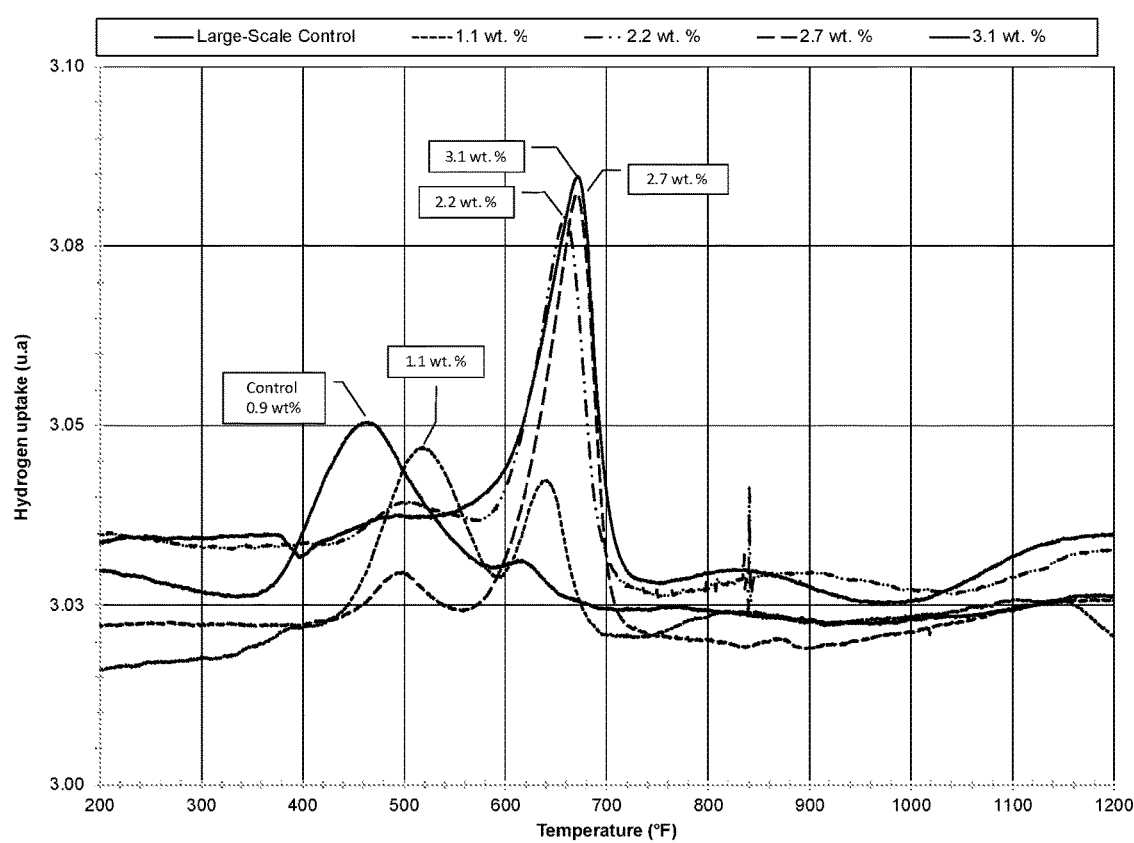
FIG. 7 presents a Temperature Programmed Reduction plot for the supported catalysts of Example 4.

In Example 4, supported catalysts were produced as described in Example 1, and the Cl contents were 1.1 wt. %, 2.2 wt. %, 2.7 wt. %, and 3.1 wt. %. FIG. 7 is a Temperature Programmed Reduction (TPR) plot for the supported catalysts containing ~0.9 wt. % Cl (Large-Scale Control), 1.1 wt. % Cl, 2.2 wt. % Cl, 2.7 wt. % Cl, and 3.1 wt. % Cl.

From a comparison of the high chlorine content supported catalysts (2.2-3.1 wt. %) with the low chlorine content supported catalysts (0.9-1.1 wt. %), a few general trends are observed. First, the peak temperatures (the temperature of the highest peak on the curve) are significantly higher for the high chlorine content supported catalysts as compared to the low chlorine content supported catalysts. Second, as to the relative heights of the peaks, the higher temperature peak for the high chlorine content supported catalysts is larger than the lower temperature peak, while for the low chlorine content supported catalysts, the opposite is true. Table II summarizes the respective peak temperature and temperature of the second largest peak from the plots in FIG. 7.

TABLE II

Example 4-TPR summary.

| Chlorine (wt. %) | TPR Peak Temperature (° F.) | Second Largest TPR Peak Temperature (° F.) |
|---|---|---|
| 0.85 Large-Scale Control | 464 | 614 |
| 1.1 | 518 | 636 |
| 2.2 | 658 | 500 |
| 2.7 | 670 | 497 |
| 3.1 | 670 | 492 |

Example 5

In Example 5, a supported catalyst was produced as described in Example 1, and the Cl content was 2.7 wt. %. This catalyst was evaluated against the Large-Scale Control catalyst (0.85 wt. % Cl), for long-term activity and stability performance, and catalyst fouling rate. For this 2500-hr test, 80 cc of the supported catalyst was reduced in 10 mol % hydrogen in nitrogen, then a feed stream of aliphatic hydrocarbons and molecular hydrogen was introduced to a 1" reactor containing the catalyst at a pressure of 65 psig, a hydrogen:hydrocarbon ratio of 2:1, and a LHSV=1.6 hr$^{-1}$ to obtain catalyst performance data over time. The total yield of aromatics was maintained at 83.5 wt. % over the 2500 hr run by adjusting the temperature to maintain the desired yield, as described above.

Figure 8:
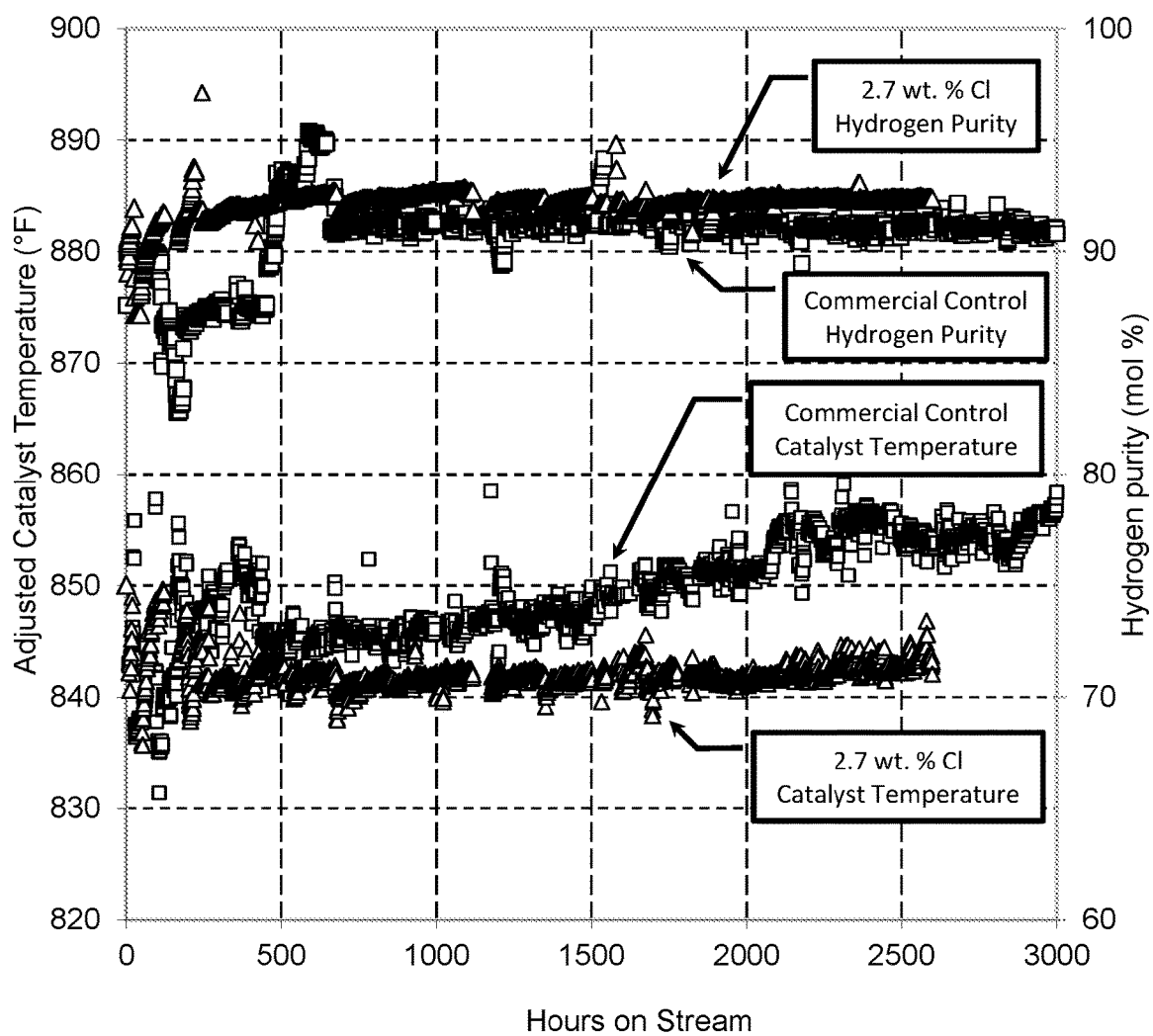
FIG. 8 presents a plot of the yield-adjusted temperature and hydrogen purity versus reaction time for the supported catalysts of Example 5.

FIG. 8 compares the yield-adjusted temperature versus the reaction time for each catalyst. As shown in the figure, the high chlorine content supported catalyst (2.7 wt. %), unexpectedly, had superior performance: higher catalyst activities throughout the 2500-hr run (lower $T_{SOR}$ and $T_{EOR}$) and a lower fouling rate, indicative of a higher stability catalyst.

Example 6

In Example 6, a supported catalyst was produced as described in Example 1, and the Cl content was 2.7 wt. %. This catalyst was evaluated against the Large-Scale Control catalyst. These catalysts were subjected to a controlled reduction step at 950° F. for 1 hour with 100% $H_2$ to determine the amount of Cl that remains after the reduction step. Table III summarizes the results. While the F content is relatively unchanged, the Cl content and N content, surprisingly, are reduced significantly from the respective amounts present in the supported aromatization catalyst, prior to a reduction (or activation) step.

TABLE III

Example 6-Catalyst property summary.

| Catalyst | F (wt. %) | Cl (wt. %) | Cl (% loss) | N (wt. %) |
|---|---|---|---|---|
| Large-Scale Control | 0.54 | 0.34 | 62 | 0.01 |
| High Cl | 0.53 | 0.40 | 85 | 0.01 |

Example 7

Figure 9:
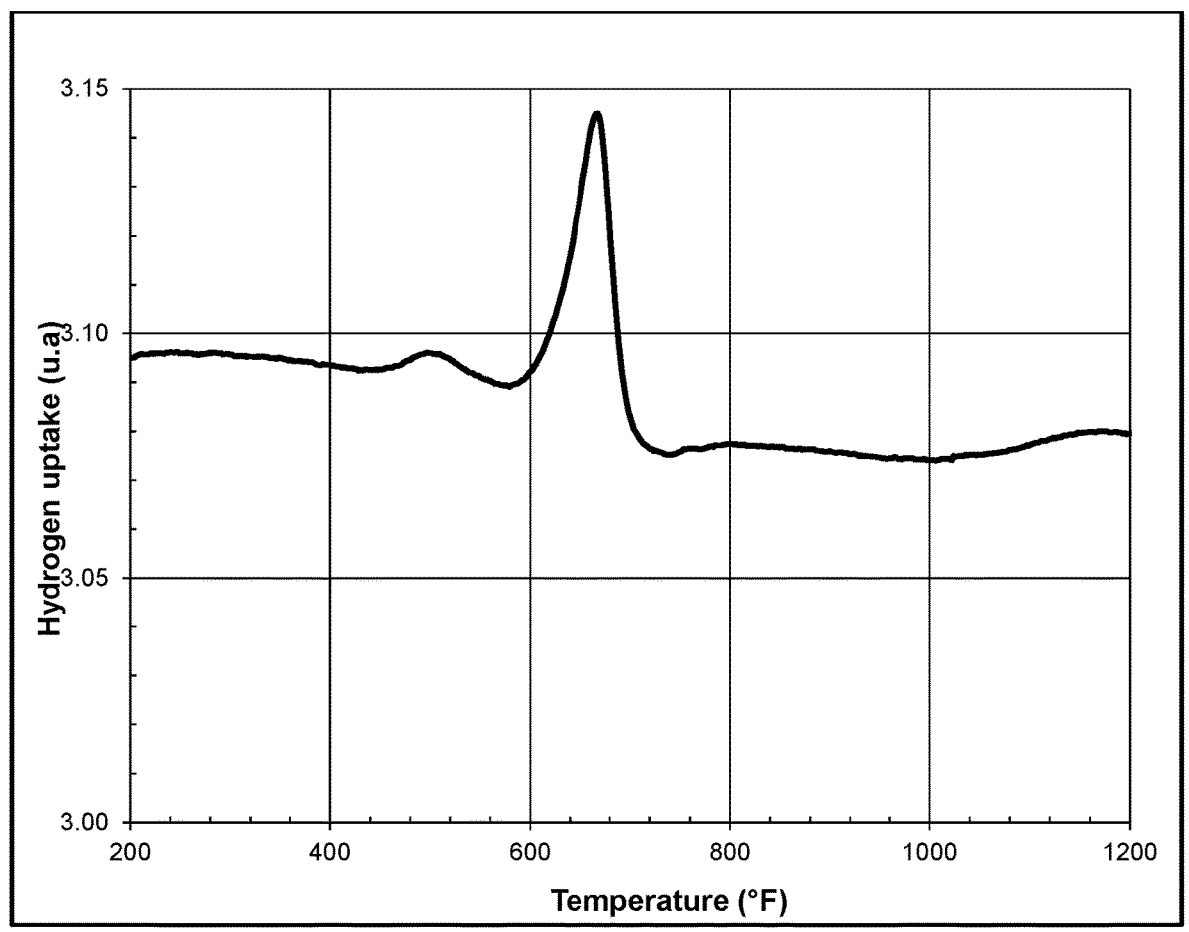
FIG. 9 presents a Temperature Programmed Reduction plot for the high chlorine supported catalyst of Example 7.

In Example 7, a supported catalyst was produced as described in Example 1, and the Pt content was ~1 wt. % and the Cl content was 2.5 wt. %. Table IV summarizes the catalyst properties of the high chlorine content catalyst and that of the Large-Scale Control catalyst. The platinum content, platinum dispersion, surface area, and F content of these catalysts were substantially the same, while the Cl and N contents were significantly higher for the high chlorine content catalyst (2.5 wt. % Cl). FIG. 9 is a Temperature Programmed Reduction (TPR) plot for the supported catalyst containing 2.5 wt. % Cl. The peak temperature was approximately 668° F., and the temperature of the second largest peak was approximately 490° F. These temperatures are consistent with the high chlorine content catalysts evaluated in Example 4 (see Table II and FIG. 7).

Figure 10:
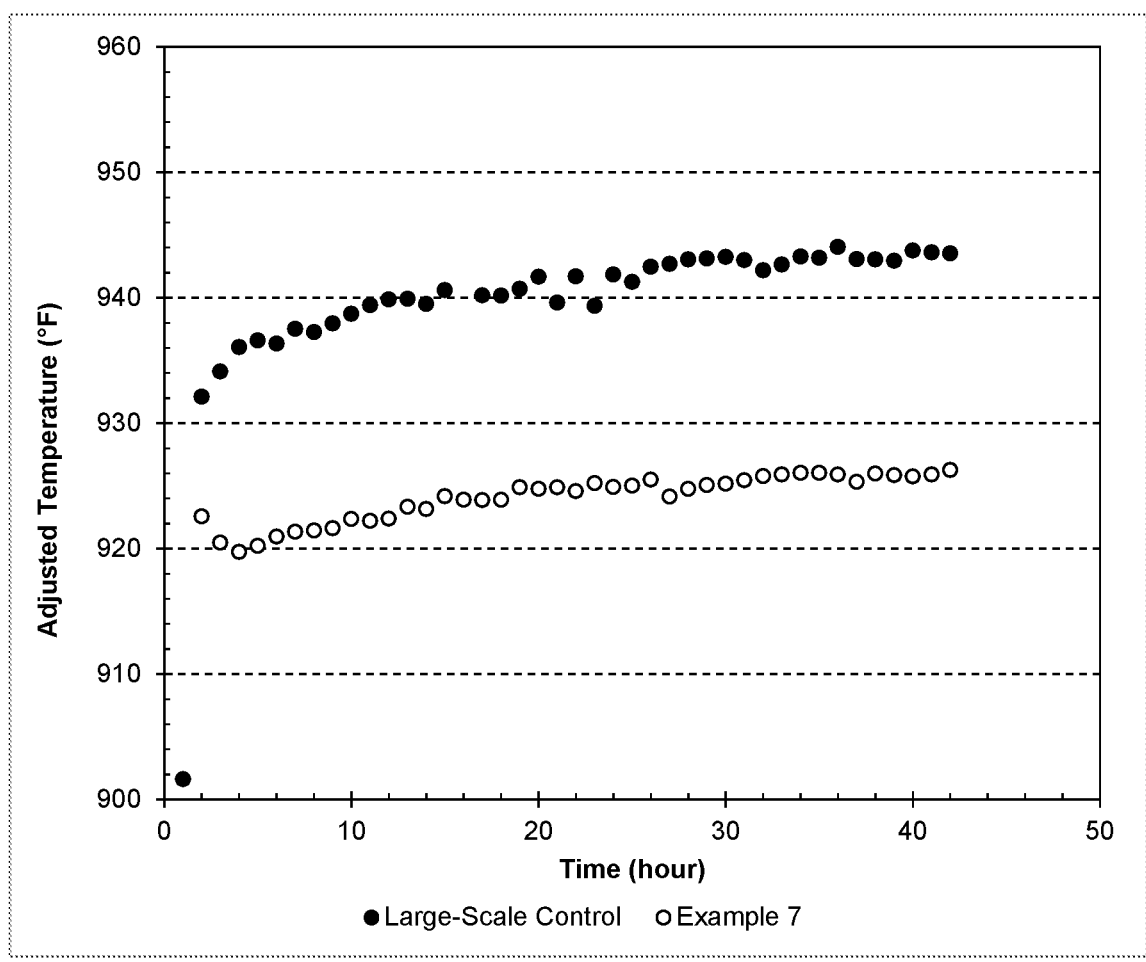
FIG. 10 presents a plot of the yield-adjusted temperature versus reaction time for the control catalyst and high chlorine supported catalyst of Example 7.

FIG. 10 compares the yield-adjusted temperature versus the reaction time for the Large-Scale Control catalyst and the high chlorine content catalyst (2.5 wt. % Cl). The 40-hour test procedure in Example 3 was used, with the exception that the total yield of aromatics (such as benzene and toluene) was maintained at 66 wt. % over time at the standard test conditions. Table V summarizes the relevant catalyst performance metrics from FIG. 10. As shown in the table and figure, the high chlorine content supported catalyst (2.5 wt. %), unexpectedly, had far superior performance to that of the control catalyst: higher catalyst activity (lower $T_{SOR}$ and $T_{EOR}$) and a lower fouling rate. Interestingly, these beneficial results were achieved without significant changes in the platinum content, platinum dispersion, surface area, and F content of the catalyst.

TABLE IV

Example 7-Catalyst property summary.

| Chlorine (wt. %) | F (wt. %) | N (wt. %) | Surface Area (m²/g) | Platinum Dispersion (%) |
|---|---|---|---|---|
| 0.85 Large-Scale Control | 0.71 | 0.3 | 177 | 67 |
| 2.5 | 0.70 | 1.0 | 170 | 67 |

TABLE V

Example 7-Catalyst performance summary.

| Chlorine (wt. %) | $T_{SOR}$ (° F.) | $T_{EOR}$ (° F.) | Fouling Rate (° F./hr.) |
|---|---|---|---|
| 0.85 Large-Scale Control | 938 | 944 | 0.14 |
| 2.5 | 923 | 926 | 0.08 |

The invention is described above with reference to numerous aspects and specific examples. Many variations will suggest themselves to those skilled in the art in light of the above detailed description. All such obvious variations are within the full intended scope of the appended claims. Other aspects of the invention may include, but are not limited to, the following (aspects are described as "comprising" but, alternatively, may "consist essentially of" or "consist of"):

Aspect 1. A method of producing a supported catalyst, the method comprising:

(a) impregnating a bound zeolite base with a transition metal precursor, a chlorine precursor, and a fluorine precursor to form an impregnated zeolite base; and (b) drying and then calcining the impregnated zeolite base to produce the supported catalyst; wherein the supported catalyst comprises, based on the total weight of the supported catalyst:

from about 0.3 wt. % to about 3 wt. % of a transition metal;

from about 1.8 wt. % to about 4 wt. % of chlorine; and from about 0.4 wt. % to about 1.5 wt. % of fluorine; and wherein the supported catalyst is characterized by a peak reduction temperature on a Temperature Programmed Reduction curve in a range from about 580° F. to about 800° F.

Aspect 2. The method defined in aspect 1, wherein the bound zeolite base is produced by a process comprising:

combining a zeolite with a binder to form a mixture, and extruding the mixture to form an extrudate;

drying and calcining the extrudate to form a calcined base; and washing, drying, and calcining the calcined base to form the bound zeolite base.

Aspect 3. The method defined in aspect 1 or 2, wherein drying and then calcining the impregnated zeolite base comprises any suitable drying conditions or any drying conditions disclosed herein, e.g., a drying temperature in a range from about 50° C. to about 200° C., or from about 80° C. to about 150° C., and drying at atmospheric pressure or sub-atmospheric pressure, e.g., less than about 150 Torr, or less than about 50 Torr.

Aspect 4. The method defined in any one of the preceding aspects, wherein drying and then calcining the impregnated zeolite base comprises any suitable calcining conditions or any calcining conditions disclosed herein, e.g., a peak calcining temperature in a range from about 200° C. to about 500° C., or from about 230° C. to about 350° C., and in a calcining gas stream comprising nitrogen, oxygen, air, or any combination thereof.

Aspect 5. The method defined in any one of the preceding aspects, wherein the method further comprises a reducing step after the drying and calcining of the impregnated zeolite base, the reducing step comprising contacting the supported catalyst with any suitable reducing gas stream or any reducing gas stream disclosed herein (e.g., comprising hydrogen) to produce a reduced (or activated) supported catalyst.

Aspect 6. The method defined in aspect 5, wherein the reducing step is conducted at any suitable reducing temperature or any reducing temperature disclosed herein, e.g., in a range from about 100° C. to about 700° C., or from about 200° C. to about 600° C.

Aspect 7. The method defined in any one of the preceding aspects, wherein impregnating the bound zeolite base with the transition metal precursor comprises mixing the bound zeolite base with any suitable transition metal precursor or any transition metal precursor disclosed herein, e.g., tetraamineplatinum(II) chloride, tetraamineplatinum(II)

nitrate, platinum(II) acetylacetonate, platinum(II) chloride, ammonium tetrachloroplatinate(II), chloroplatinic acid, platinum (II) nitrate, or a combination thereof.

Aspect 8. The method defined in any one of the preceding aspects, wherein impregnating the bound zeolite base with the chlorine precursor and the fluorine precursor comprises mixing the bound zeolite base with any suitable chlorine precursor and/or fluorine precursor, or any chlorine precursor and/or fluorine precursor disclosed herein, e.g., ammonium chloride, tetramethylammonium chloride, tetraethyl ammonium chloride, tetrapropylammonium chloride, tetrabutylammonium chloride, methyltriethylammonium chloride, ammonium fluoride, tetramethylammonium fluoride, tetraethylammonium fluoride, tetrapropylammonium fluoride, tetrabutylammonium fluoride, methyltriethylammonium fluoride, or a combination thereof.

Aspect 9. The method defined in any one of the preceding aspects, wherein impregnating the bound zeolite base with the transition metal precursor, chlorine precursor, and fluorine precursor comprises mixing the bound zeolite base with an aqueous solution comprising the transition metal precursor, the chlorine precursor, and/or the fluorine precursor.

Aspect 10. A supported catalyst obtained by the method defined in any one of the preceding aspects, e.g., a supported aromatization catalyst.

Aspect 11. A supported catalyst comprising:
a bound zeolite base;
from about 0.3 wt. % to about 3 wt. % of a transition metal;
from about 1.8 wt. % to about 4 wt. % of chlorine; and
from about 0.4 wt. % to about 1.5 wt. % of fluorine; based on the total weight of the supported catalyst; and wherein
the supported catalyst is characterized by a peak reduction temperature on a Temperature Programmed Reduction curve in a range from about 580° F. to about 800° F.

Aspect 12. The catalyst or method defined in any one of the preceding aspects, wherein the supported catalyst comprises any weight percentage of chlorine disclosed herein, e.g., from about 2 wt. % to about 3.8 wt. %, from about 2.2 wt. % to about 3.6 wt. %, from about 2.2 wt. % to about 3.4 wt. %, or from about 2.5 wt. % to about 3.3 wt. % chlorine.

Aspect 13. The catalyst or method defined in any one of the preceding aspects, wherein the supported catalyst comprises any weight percentage of fluorine disclosed herein, e.g., from about 0.5 wt. % to about 1.3 wt. %, from about 0.5 wt. % to about 1.1 wt. %, or from about 0.6 wt. % to about 0.9 wt. % fluorine.

Aspect 14. The catalyst or method defined in any one of the preceding aspects, wherein the bound zeolite base (or the supported catalyst) comprises a zeolite and a binder.

Aspect 15. The catalyst or method defined in aspect 14, wherein the bound zeolite base (or the supported catalyst) comprises any weight percentage of binder disclosed herein, e.g., from about 3 wt. % to about 35 wt. %, or from about 5 wt. % to about 30 wt. % binder, based on the total weight of the bound zeolite base (or the supported catalyst).

Aspect 16. The catalyst or method defined in aspect 14 or 15, wherein the binder comprises an inorganic solid oxide, a clay, or a combination thereof.

Aspect 17. The catalyst or method defined in aspect 14 or 15, wherein the binder comprises alumina, silica, magnesia, boria, titania, zirconia, a mixed oxide thereof, or a mixture thereof.

Aspect 18. The catalyst or method defined in aspect 14 or 15, wherein the binder comprises silica.

Aspect 19. The catalyst or method defined in any one of the preceding aspects, wherein the bound zeolite base (or the supported catalyst) comprises a bound L-zeolite.

Aspect 20. The catalyst or method defined in any one of aspects 1-18, wherein the bound zeolite base (or the supported catalyst) comprises a bound barium ion-exchanged L-zeolite.

Aspect 21. The catalyst or method defined in any one of aspects 1-18, wherein the bound zeolite base (or the supported catalyst) comprises a bound K/L-zeolite.

Aspect 22. The catalyst or method defined in any one of aspects 1-17, wherein the bound zeolite base (or the supported catalyst) comprises a silica-bound K/L-zeolite Aspect 23. The catalyst or method defined in aspect 22, wherein the bound zeolite base is produced by a process comprising:
combining a K/L-zeolite with a silica sol to form a mixture, extruding the mixture to form an extrudate,
drying, and calcining the extrudate to form a calcined base; and
washing, drying, and calcining the calcined base to form the bound zeolite base.

Aspect 24. The catalyst or method defined in any one of the preceding aspects, wherein the supported catalyst comprises any weight percentage of transition metal disclosed herein, e.g., from about 0.5 wt. % to about 2.5 wt. %, from about 0.5 wt. % to about 2 wt. %, or from about 0.7 wt. % to about 1.5 wt. % transition metal.

Aspect 25. The catalyst or method defined in any one of the preceding aspects, wherein the transition metal comprises platinum.

Aspect 26. The catalyst or method defined in any one of the preceding aspects, wherein the supported catalyst comprises any weight percentage of platinum disclosed herein, e.g., from about 0.5 wt. % to about 2.5 wt. %, from about 0.5 wt. % to about 2 wt. %, or from about 0.7 wt. % to about 1.5 wt. % platinum.

Aspect 27. The catalyst or method defined in any one of the preceding aspects, wherein the supported catalyst is characterized by a peak temperature on a TPR curve in any range disclosed herein, e.g., from about 580° F. to about 750° F., from about 600° F. to about 730° F., or from about 600° F. to about 720° F.

Aspect 28. The catalyst or method defined in any one of the preceding aspects, wherein the supported catalyst is characterized by a TPR curve comprising a lower temperature peak and a higher temperature peak, and wherein the higher temperature peak is greater in height than the lower temperature peak.

Aspect 29. The catalyst or method defined in any one of the preceding aspects, wherein the supported catalyst comprises any weight ratio of chlorine:fluorine disclosed herein, e.g., from about 1.5:1 to about 8:1, from about 2:1 to about 5:1, or from about 3:1 to about 4.5:1.

Aspect 30. The catalyst or method defined in any one of aspects 6-31, wherein the reduced (or activated) supported catalyst comprises any weight percentage of chlorine disclosed herein, e.g., from about 0.2 wt. % to about 1.3 wt. %, from about 0.2 wt. % to about 0.8 wt. %, or from about 0.3 wt. % to about 1 wt. % chlorine, based on the total weight of the reduced (or activated) supported catalyst.

Aspect 31. The catalyst or method defined in any one of the preceding aspects, wherein the supported catalyst has a platinum dispersion that is substantially the same as that of a catalyst having from 0.3 wt. % to 1.5 wt. % chlorine, under the same catalyst preparation conditions.

Aspect 32. The catalyst or method defined in any one of the preceding aspects, wherein the supported catalyst has a surface area that is substantially the same as that of a catalyst having from 0.3 wt. % to 1.5 wt. % chlorine, under the same catalyst preparation conditions.

Aspect 33. The catalyst or method defined in any one of the preceding aspects, wherein the supported catalyst has a total nitrogen content that is greater than that of a catalyst having from 0.3 wt. % to 1.5 wt. % chlorine, under the same catalyst preparation conditions (by any amount disclosed herein, e.g., at least about 50% greater, at least about 100% greater, or at least about 200% greater).

Aspect 34. The catalyst or method defined in any one of the preceding aspects, wherein the supported catalyst is characterized by a $T_{EOR}$ (end of run temperature) in any range disclosed herein, e.g., from about 920° F. to about 940° F., or from about 920° F. to about 930° F.

Aspect 35. The catalyst or method defined in any one of the preceding aspects, wherein the supported catalyst is characterized by a $T_{EOR}$ less than that of a catalyst having from 0.3 wt. % to 1.5 wt. % chlorine, under the same catalyst preparation and aromatization reaction conditions.

Aspect 36. The catalyst or method defined in any one of the preceding aspects, wherein the supported catalyst is characterized by a $T_{SOR}$ (start of run temperature) in any range disclosed herein, e.g., from about 915° F. to about 935° F., or from about 915° F. to about 930° F.

Aspect 37. The catalyst or method defined in any one of the preceding aspects, wherein the supported catalyst is characterized by a $T_{SOR}$ less than that of a catalyst having from 0.3 wt. % to 1.5 wt. % chlorine, under the same catalyst preparation and aromatization reaction conditions.

Aspect 38. The catalyst or method defined in any one of the preceding aspects, wherein the supported catalyst is characterized by a Fouling Rate in any range disclosed herein, e.g., less than about 0.12° F./min, or less than about 0.1° F./min.

Aspect 39. The catalyst or method defined in any one of the preceding aspects, wherein the supported catalyst is characterized by a Fouling Rate less than that of a catalyst having from 0.3 wt. % to 1.5 wt. % chlorine, under the same catalyst preparation and aromatization reaction conditions.

Aspect 40. The catalyst or method defined in any one of the preceding aspects, wherein the supported catalyst is characterized by an aromatics selectivity (or a benzene+ toluene selectivity) that is substantially the same as that of a catalyst having from 0.3 wt. % to 1.5 wt. % chlorine, under the same catalyst preparation and aromatization reaction conditions.

Aspect 41. A reforming process comprising contacting a hydrocarbon feed with a supported aromatization catalyst under reforming conditions in a reactor system to produce an aromatic product, wherein the supported aromatization catalyst is the supported catalyst (or the reduced or activated catalyst) defined in any one of the preceding aspects.

Aspect 42. The process defined in aspect 41, wherein the hydrocarbon feed is any hydrocarbon feed disclosed herein, e.g., comprising non-aromatic hydrocarbons, comprising $C_6$-$C_9$ alkanes and/or cycloalkanes, or comprising $C_6$-$C_8$ alkanes and/or cycloalkanes.

I claim:

1. A supported catalyst comprising:
a bound zeolite base, wherein the bound zeolite base comprises a binder and a large pore zeolite having an average pore diameter in a range of from about 7 Å to about 12 Å;
from about 0.7 wt. % to about 1.5 wt. % of platinum, based on the total weight of the supported catalyst;
from about 2 wt. % to about 3.3 wt. % of chlorine, based on the total weight of the supported catalyst; and
from about 0.5 wt. % to about 1.3 wt. % of fluorine, based on the total weight of the supported catalyst;
wherein the supported catalyst is characterized by a peak reduction temperature on a Temperature Programmed Reduction curve in a range from about 600° F. to about 720° F.

2. The catalyst of claim 1, wherein the bound zeolite base comprises from about 10 wt. % to about 30 wt. % of the binder, based on the total weight of the bound zeolite base.

3. The catalyst of claim 1, wherein a weight ratio of chlorine:fluorine is in a range from about 3:1 to about 4.5:1.

4. The catalyst of claim 1, wherein the supported catalyst is characterized by a Temperature Programmed Reduction curve comprising a lower temperature peak and a higher temperature peak, and wherein the higher temperature peak is greater in height than the lower temperature peak.

5. The catalyst of claim 1, wherein the supported catalyst further comprises from about 0.7 wt. % to about 1.2 wt. % nitrogen based on the total weight of the supported catalyst.

6. A supported catalyst comprising:
a bound zeolite base comprising a silica-bound K/L-zeolite;
from about 0.7 wt. % to about 1.5 wt. % of platinum, based on the total weight of the supported catalyst;
from about 2 wt. % to about 3.3 wt. % of chlorine, based on the total weight of the supported catalyst; and
from about 0.5 wt. % to about 1.1 wt. % of fluorine, based on the total weight of the supported catalyst;
wherein the supported catalyst is characterized by a peak reduction temperature on a Temperature Programmed Reduction curve in a range from about 600° F. to about 730° F.

7. The catalyst of claim 6, wherein the supported catalyst is characterized by a Temperature Programmed Reduction curve comprising a lower temperature peak and a higher temperature peak, and wherein the higher temperature peak is greater in height than the lower temperature peak.

8. The catalyst of claim 7, wherein the peak reduction temperature is in a range from about 630° F. to about 690° F.

9. The catalyst of claim 8, wherein a weight ratio of chlorine:fluorine is in a range from about 3:1 to about 4.5:1.

10. The catalyst of claim 6, wherein the bound zeolite base comprises from about 10 wt. % to about 30 wt. % of a silica binder, based on the total weight of the bound zeolite base.

11. The catalyst of claim 10, wherein the supported catalyst further comprises from about 0.7 wt. % to about 1.2 wt. % nitrogen based on the total weight of the supported catalyst.

12. The catalyst of claim 6, wherein:
the supported catalyst further comprises from about 0.6 wt. % to about 1.3 wt. % nitrogen; and
the peak reduction temperature is in a range from about 630° F. to about 690° F. based on the total weight of the supported catalyst.

13. The catalyst of claim 12, wherein:
the supported catalyst comprises from about 0.7 wt. % to about 1.2 wt. % nitrogen;
a weight ratio of chlorine:fluorine is in a range from about 3:1 to about 4.5:1; and
the bound zeolite base comprises from about 10 wt. % to about 30 wt. % of a silica binder, based on the total weight of the bound zeolite base based on the total weight of the supported catalyst.

14. A reforming process comprising:
(i) contacting a supported catalyst with a reducing gas stream to produce an activated aromatization catalyst, wherein the supported catalyst comprises:
a bound zeolite base, wherein the bound zeolite base comprises a binder and a large pore zeolite having an average pore diameter in a range of from about 7 Å to about 12 Å;
from about 0.7 wt. % to about 1.5 wt. % of platinum, based on the total weight of the supported catalyst;
from about 2 wt. % to about 3.3 wt. % of chlorine, based on the total weight of the supported catalyst; and
from about 0.5 wt. % to about 1.3 wt. % of fluorine, based on the total weight of the supported catalyst;
wherein the supported catalyst is characterized by a peak reduction temperature on a Temperature Programmed Reduction curve in a range from about 600° F. to about 720° F.; and
(ii) contacting a hydrocarbon feed with the activated aromatization catalyst under reforming conditions in a reactor system to produce an aromatic product.

15. The process of claim 14, wherein the step (i) comprising contacting the supported catalyst with the reducing gas stream at a reducing temperature in a range from about 100° C. to about 700° C. to produce the activated aromatization catalyst, wherein the reducing gas stream comprises hydrogen.

16. The process of claim 14, wherein the hydrocarbon feed comprises $C_6$-$C_9$ alkanes and/or cycloalkanes.

17. The process of claim 14, wherein the activated aromatization catalyst comprises from about 0.3 wt. % to about 1 wt. % of chlorine, based on the total weight of the activated aromatization catalyst.

18. The process of claim 14, wherein the bound zeolite base comprises a silica-bound K/L-zeolite.

19. The process of claim 18, wherein:
the supported catalyst is characterized by a Temperature Programmed Reduction curve comprising a lower temperature peak and a higher temperature peak, and wherein the higher temperature peak is greater in height than the lower temperature peak; and
the peak reduction temperature is in a range from about 630° F. to about 690° F.

20. The process of claim 19, wherein the activated aromatization catalyst comprises from about 0.2 wt. % to about 0.8 wt. % of chlorine, based on the total weight of the activated aromatization catalyst.

* * * * *